(12) United States Patent
Mitusina

(10) Patent No.: US 7,803,170 B2
(45) Date of Patent: Sep. 28, 2010

(54) ROTARY SURGICAL INSTRUMENTS HAVING CURVED CUTTING TEETH

(75) Inventor: Miro Mitusina, Ruskin, FL (US)

(73) Assignee: B&M Precision, Inc., Ruskin, FL (US)

( * ) Notice: Subject to any disclaimer, the term of this patent is extended or adjusted under 35 U.S.C. 154(b) by 467 days.

(21) Appl. No.: 11/707,748

(22) Filed: Feb. 16, 2007

(65) Prior Publication Data

US 2008/0200941 A1     Aug. 21, 2008

(51) Int. Cl.
   *A61B 17/32* (2006.01)
(52) U.S. Cl. .................................... 606/171; 606/180
(58) Field of Classification Search ................ 604/22; 606/170–171, 167–180
   See application file for complete search history.

(56) References Cited

U.S. PATENT DOCUMENTS

| | | | |
|---|---|---|---|
| 2,172,786 A * | 9/1939 | Bishir | ................ 56/238 |
| 3,732,858 A | 5/1973 | Banko | |
| 4,203,444 A | 5/1980 | Bonnell et al. | |
| 4,649,919 A | 3/1987 | Thimsen et al. | |
| 4,867,157 A | 9/1989 | McGurk-Burleson et al. | |
| 5,007,917 A | 4/1991 | Evans | |
| 5,084,052 A | 1/1992 | Jacobs | |
| 5,123,904 A | 6/1992 | Shimomura et al. | |
| 5,346,020 A * | 9/1994 | Bassett | ................ 172/540 |
| 5,383,884 A | 1/1995 | Summers | |
| 5,593,416 A * | 1/1997 | Donahue | ................ 606/170 |
| 5,759,185 A | 6/1998 | Grinberg | |
| 5,833,692 A | 11/1998 | Cesarini et al. | |
| 5,922,003 A * | 7/1999 | Anctil et al. | ................ 606/170 |
| 6,217,598 B1 | 4/2001 | Berman et al. | |
| 6,342,061 B1 | 1/2002 | Kauker et al. | |
| 6,419,684 B1 | 7/2002 | Heisler et al. | |
| 6,533,749 B1 | 3/2003 | Mitusina et al. | |
| 6,620,180 B1 | 9/2003 | Bays et al. | |
| 2006/0196038 A1* | 9/2006 | Van Wyk | ................ 29/557 |

* cited by examiner

*Primary Examiner*—Anhtuan T Nguyen
*Assistant Examiner*—Ashley Cronin

(57) ABSTRACT

A rotary surgical instrument includes an outer member having an aperture in a distal portion thereof, and an inner member for being rotatably disposed within the outer member to move a cutting element on the inner member past the aperture to cut anatomical tissue. The inner member has an aperture, and the cutting element comprises first and second rows of cutting teeth extending longitudinally along opposite sides of the inner member aperture. Each cutting tooth is convexly curved, the cutting teeth of one row curving in opposition to the cutting teeth of the other row. The rows of cutting teeth have their tips staggered.

27 Claims, 7 Drawing Sheets

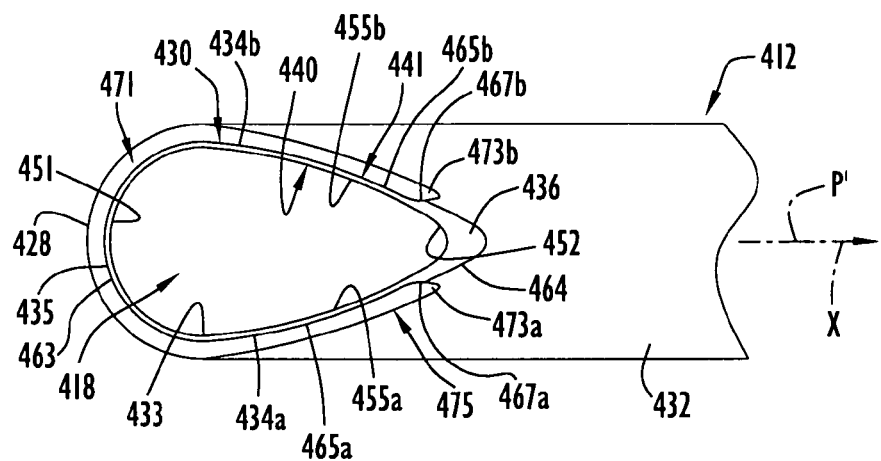
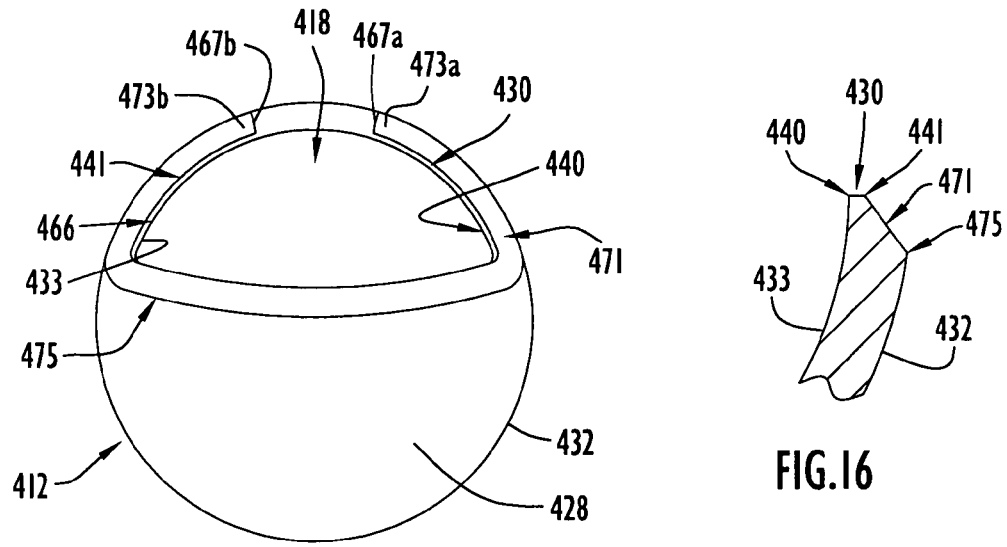
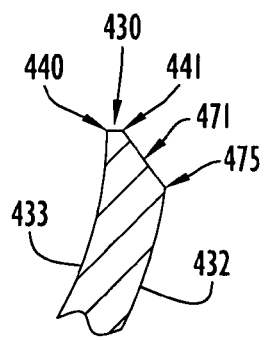
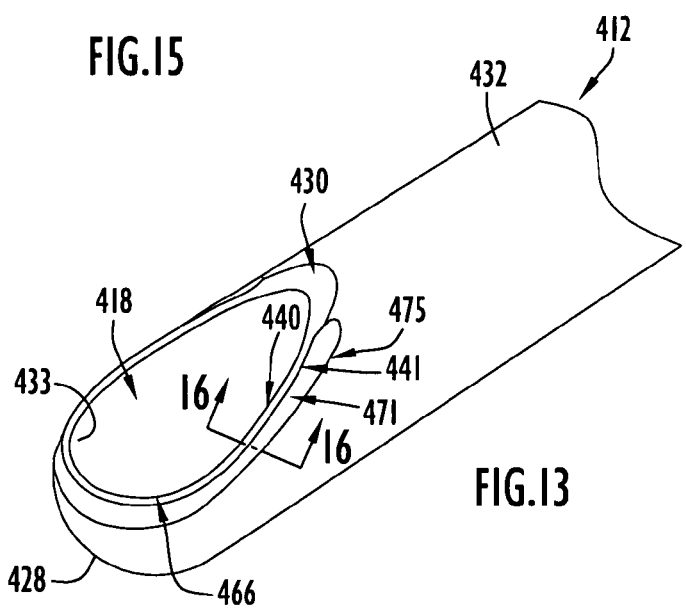

ROTARY SURGICAL INSTRUMENTS HAVING CURVED CUTTING TEETH

BACKGROUND OF THE INVENTION

1. Field of the Invention

The present invention relates generally to rotary surgical instruments having an inner member rotatably disposed within an outer member such that a cutting element on the inner member rotates past an aperture in the outer member to cut anatomical tissue positioned in the aperture. More particularly, the invention pertains to rotary surgical instruments in which the cutting element of the inner member comprises a plurality of cutting teeth.

2. Brief Discussion of the Related Art

Rotary surgical instruments are commonly employed in various surgical procedures to cut anatomical tissue at an operative site. Rotary surgical instruments are especially advantageous for use in endoscopic or minimally invasive surgical procedures where access to the operative site is gained via a narrow or relatively small size portal or incision. Rotary surgical instruments typically comprise an elongate tubular outer member and an elongate inner member rotatably disposed within the outer member. A distal end of the tubular outer member ordinarily has a side-facing aperture or window providing communication with the internal lumen of the outer member. The inner member is rotatably disposed within the internal lumen of the outer member, and a distal end of the inner member has a cutting element that rotates past the aperture in the outer member to cut anatomical tissue positioned in the aperture. Proximal ends of the outer and inner members are conventionally attached to respective hubs for being coupled with a powered surgical handpiece. The outer member hub is ordinarily coupled with the handpiece to hold the outer member in a fixed or stationary position. The inner member hub is ordinarily coupled with the drive shaft of a motor of the handpiece, which rotates the inner member relative to and within the outer member to rotate the cutting element past the aperture. In many rotary surgical instruments, irrigating fluid is supplied to the operative site through an irrigation passage defined by an annular gap or clearance between the outer and inner members.

It is conventional for the inner member of rotary surgical instruments to be tubular and for the distal end of the inner member to have a side-facing aperture or window that provides communication with the internal lumen of the inner member. The aperture in the inner member repetitively comes into rotational alignment with the aperture in the outer member as the inner member rotates within the outer member. The internal lumen of the inner member may be coupled with a suction source to serve as a suction or aspiration passage providing suction or aspiration at the operative site via the rotationally aligned apertures to evacuate fluid and anatomical tissue.

The aperture in the inner member is normally circumscribed by a peripheral surface, and the cutting element of the inner member is commonly formed by a sharp cutting edge of the peripheral surface of the inner member aperture. Similarly, the aperture in the outer member is commonly circumscribed by a peripheral surface, and the outer member is typically provided with a cutting element formed by a sharp cutting edge of the peripheral surface of the outer member aperture to cooperate with the cutting edge of the inner member to cut anatomical tissue. In some rotary surgical instruments, the outer member cutting element includes two straight cutting edges, i.e. cutting edges without a toothed configuration, respectively extending longitudinally along opposite sides of the outer member aperture. The opposite sides of the outer member aperture may follow the path of an oblique or angled plane in profile as represented by U.S. Pat. No. 6,342,061 to Kauker et al and U.S. Pat. No. 5,383,884 to Summers. The opposite sides of the outer member aperture may follow an arcuate or curved path in profile as illustrated by U.S. Pat. No. 3,732,858 to Banko. The inner member cutting element oftentimes includes two straight cutting edges, i.e. cutting edges without a toothed configuration, respectively extending longitudinally along opposite sides of the inner member aperture. The opposite sides of the inner member aperture may similarly follow the path of an oblique or angled plane or may follow an arcuate or curved path in profile. Typically the cutting edges are formed by grinding the tubular member to obtain the requisite sharpness. Rotary surgical instruments of the latter type are generally known as a "full radius" design. Rotary surgical instruments that provide a more aggressive cutting action over a "full radius" design are those in which the cutting element of the outer member comprises two straight cutting edges as in the "full radius" design, while the cutting element of the inner member includes two rows of cutting teeth respectively extending longitudinally along the opposite sides of the inner member aperture. The most aggressive cutting action is generally obtained with rotary surgical instruments in which the cutting element of each of the outer and inner members includes two rows of cutting teeth respectively extending longitudinally along the opposite sides of its aperture as represented by U.S. Pat. No. 6,533,749 B1 to Mitusina et al.

In rotary surgical instruments where at least the inner member cutting element is comprised of two rows of cutting teeth, the peripheral surface of the inner member aperture is typically configured to form a distal side and a proximal side of each cutting tooth which define the geometric profile of the cutting tooth. In many cases, the cutting teeth are formed to have a flat or planar distal side and a flat or planar proximal side extending upwardly from a base or root of the cutting tooth to a tip of the cutting tooth. It is common for the distal and proximal sides of the cutting teeth to define a triangular geometric profile. The included angle defined between the distal and proximal sides of the cutting teeth is commonly in the range of 600 to 1000. Sometimes the cutting teeth are formed with sides that curve concavely from the root to the tip of the cutting tooth.

In cases where the inner member cutting element comprises two rows of cutting teeth, the distal sides of the cutting teeth of one row are usually the same as the distal sides of the cutting teeth of the opposite row. The proximal sides of the cutting teeth of one row are also usually the same as the proximal sides of the cutting teeth of the opposite row, such that the cutting teeth of one row have the same geometric profile as the cutting teeth of the opposite row. In addition, the tips of the cutting teeth of one row are normally aligned with the tips of the cutting teeth of the opposite row in a lateral direction perpendicular to the central longitudinal axis of the inner member. Accordingly, each row of cutting teeth provides the same cutting action, and the cutting action provided by one row of the cutting teeth is thusly duplicative of the cutting action provided by the opposite row of the cutting teeth.

The cutting teeth are normally formed by grinding the tubular inner member to create a sharp cutting edge, or knife edge, on the cutting teeth, which normally involves providing the cutting teeth with a positive relief angle. The tips of the cutting teeth usually result in fragile sharp points, and a certain amount of flat is usually required to be provided at the tips to impart some resistance to bending, breakage, deformation or distortion. However, the flat required at the tips of the cutting teeth reduces the biting action of the cutting teeth and thusly reduces their effectiveness in cutting anatomical tissue. Typically the cutting teeth increase in thickness between their tips and their roots, and the root regions of the cutting teeth provide little or no knife shearing cutting action on the anatomical tissue. Anatomical tissue is cut by the cutting teeth initially with a knife shearing action as the tips and cutting edges in the upper or tip regions of the cutting teeth shear the anatomical tissue. The anatomical tissue is then squeezed into the spaces between the lower or root regions of adjacent cutting teeth for the final cutting action, which is usually a combination of shear cutting and tearing but predominantly tearing. In rotary surgical instruments wherein the outer member cutting element also comprises two rows of cutting teeth, the outer member cutting teeth are ordinarily formed in a similar manner and have similar characteristics as the inner member cutting teeth.

Conventional rotary surgical instruments of the aforementioned types have various disadvantages. Rotary surgical instruments having a "full radius" design require high torque and force to cut anatomical tissue, and the shearing load on the cutting edges is distributed over a relatively small area as limited by the length of the straight cutting edges for a given size aperture. In rotary surgical instruments where at least the inner member cutting element comprises two rows of cutting teeth, the geometric profile of the teeth is significantly underutilized for shear cutting since little or no shearing action takes place at the lower or root regions of the cutting teeth and most if not all of the shearing action takes place at the upper or tip regions of the cutting teeth. The shearing action is non-uniform or discontinuous because it is confined to and takes place over a limited or reduced portion of the geometric profile, and torque is also non-uniform or discontinuous. The limited shearing action reduces cutting effectiveness and results in the anatomical tissue being cut with greater trauma due to the squeezing and tearing of tissue that takes place in the root regions of the teeth. The fragility of the cutting teeth at their tips makes them susceptible to bending, deformation, distortion and breakage. Moreover, hoop stress within the tubular member in which the cutting teeth are formed increases the risk of distortion of the cutting teeth, particularly at the tips. Because the cutting teeth in one row have the same geometric profile, orientation and arrangement as the cutting teeth in the opposite row, their cutting action is duplicative which limits the aggressiveness of the cutting action.

It is desirable in rotary surgical instruments for the inner member to be rotatably disposed coaxially within the outer member. Oftentimes the inner member has a distal end wall in bearing contact with a distal end wall of the outer member to assist in maintaining coaxial alignment of the inner and outer members as the inner member rotates within the outer member. It is also generally desirable in rotary surgical instruments to minimize the external diameter of the outer member to reduce the size of the portal or incision needed for introduction of the instrument at the operative site. In many prior rotary surgical instruments, the geometric profile of the cutting teeth results in removal of mass or material from the tubular member above its central longitudinal axis in a large enough quantity to compromise proper axial alignment between the outer and inner members as well as proper bearing contact between the outer and inner members. Additionally, the potential for deformation arising from deficiencies in the strength and rigidity of the cutting teeth of prior rotary surgical instruments generally requires that there be greater annular clearance between the outer and inner members. Increased annular clearance between the outer and inner members usually necessitates that the external diameter of the outer member be increased, which may undesirably increase the size of the incision or portal needed for introduction of the rotary surgical instrument at the operative site. Furthermore, an increased annular clearance between the outer member and the inner member may make the inner member more susceptible to becoming axially misaligned with the outer member and may permit axial misalignments of greater magnitude.

Rotary surgical instruments that have cutting elements comprising a plurality of cutting teeth with concavely curved sides are represented by U.S. Pat. No. 5,833,692 to Cesarini et al, U.S. Pat. No. 6,217,598 B1 to Berman et al, U.S. Pat. No. 6,342,061 B1 to Kauker et al, and U.S. Pat. No. 6,419,684 B1 to Heisler et al. Cutting elements comprising a plurality of cutting teeth having concave sides as represented by the aforementioned patents generally result in removal of an even greater quantity of material or mass from the tubular member than triangular cutting teeth and are problematic for this and other reasons including fragility at the tips of the teeth, inadequate tooth strength and rigidity, limited shearing action, the potential for deformation, breakage, distortion, bending and misalignment, relatively high torque and force requirements to cut anatomical tissue, non-uniform or non-continuous shearing action and torque, and duplicative rows of cutting teeth on opposite sides of the aperture in the tubular member providing duplicative cutting action. U.S. Pat. No. 4,203,444 to Bonnell et al depicts a rotary surgical instrument in which the outer member has convexly curved formations without any tips. The convexly curved formations are not designed to cut anatomical tissue but, rather, cutting is effectuated by a helical cutting element on the inner member.

In rotary surgical instruments where the outer member is like the "full radius" design, the peripheral surface is commonly produced in the outer member along an oblique or angled plane extending through a side and distal end wall of the outer member. As a result, the peripheral surface circumscribing the aperture in the outer member has an inner peripheral edge adjoining the internal surface of the outer member and has an outer peripheral edge adjoining the external surface of the outer member. The peripheral surface has a width between the inner and outer peripheral edges and, therefore, between the internal and external surfaces of the outer member. The width of the outer member peripheral surface being defined by the full distance and cutting effectiveness of the outer member cutting element when used in combination with an inner member having a toothed cutting element.

SUMMARY OF THE INVENTION

One aspect of the present invention is generally characterized in a rotary surgical instrument comprising an elongate tubular outer member having a distal portion with an aperture, and an elongate tubular inner member for being rotatably disposed within the outer member and having cutting teeth with a sharp cutting edge along convex sides of the cutting teeth for movement past the aperture to cut anatomical tissue. The outer member includes a first cutting edge extending longitudinally along a side of the aperture and a second cutting edge extending longitudinally along an opposite side of the aperture. The inner member includes an aperture in a distal portion thereof, and the cutting teeth comprise a first row of a series of cutting teeth extending longitudinally along a side of the inner member aperture and a second row of a series of cutting teeth extending longitudinally along an opposite side of the inner member aperture. Each cutting tooth comprises a root, a tip, a convex side extending from the root to the tip, and an opposed side extending from the root to the tip. The cutting edge extends along the entire length of the convex sides from the roots to the tips of the cutting teeth. The cutting teeth are preferably formed in a thin-walled, hollow or tubular part of the distal portion of the inner member by normal laser cutting, resulting in formation of a knife-sharp cutting edge. The opposed sides of the cutting teeth may be straight or curved. The opposed sides of the cutting teeth may be convexly curved from the roots to the tips of the cutting teeth, and the opposed sides of the cutting teeth can curve convexly from the roots in the same direction as the corresponding convex sides. The cutting edge can extend along the opposed sides of the cutting teeth, and the cutting edge can extend along the entire or substantially the entire length of the opposed sides from the roots to the tips of the cutting teeth. The first and second rows of cutting teeth may extend longitudinally along the inner member in a straight longitudinal path or in a curved longitudinal path. The first and second cutting edges on the outer member may extend longitudinally along the outer member in a straight longitudinal path or in a curved longitudinal path. The first and second cutting edges on the outer member may be straight or non-toothed cutting edges, or may be toothed cutting edges. The first cutting edge may comprise a first row of a series of cutting teeth along the side of the outer member aperture, and the second cutting edge may comprise a second row of a series of cutting teeth along the opposite side of the outer member aperture. The cutting edges and cutting teeth on the outer member may be like the cutting edges and cutting teeth on the inner member, and the cutting teeth may be formed in the outer member by normal laser cutting in a thin-walled, hollow or tubular part of the distal portion of the outer member.

Another aspect of the present invention is generally characterized in a rotary surgical instrument comprising an elongate tubular outer member having a distal portion with an aperture, and an elongate tubular inner member for being rotatably disposed within the outer member and having first and second rows of cutting teeth along opposite sides of an aperture in the inner member curving convexly in opposite directions for movement past the outer member aperture to cut anatomical tissue. The outer member includes a first cutting edge extending longitudinally along a side of the outer member aperture and a second cutting edge extending longitudinally along an opposite side of the outer member aperture. The first row of cutting teeth includes a series of cutting teeth extending longitudinally along a side of the inner member aperture and the second row of cutting teeth includes a series of cutting teeth extending longitudinally along an opposite side of the inner member aperture. Each cutting tooth comprises a root and a tip, and each cutting tooth curves convexly from its root to its tip. The cutting teeth in one of the rows curve convexly in a distal direction from their roots to their tips. The cutting teeth in the other row curve convexly in the proximal direction from their roots to their tips. The first and second cutting edges on the outer member may be straight or non-toothed cutting edges, or may be toothed cutting edges as explained hereinabove for the first mentioned aspect of the invention.

A further aspect of the present invention involves a rotary surgical instrument comprising an elongate tubular outer member having a distal portion with an aperture, and an elongate tubular inner member for being rotatably disposed within the outer member and having first and second rows of cutting teeth with staggered tips along opposite sides of an aperture in the inner member for movement past the outer member aperture to cut anatomical tissue. The outer member includes a first cutting edge extending longitudinally along a side of the outer member aperture and a second cutting edge extending longitudinally along an opposite side of the outer member aperture. The first row of cutting teeth extends longitudinally along a side of the inner member aperture, and the second row of cutting teeth extends longitudinally along an opposite side of the inner member aperture. Each cutting tooth extends from a root to a tip of the cutting tooth. The tips of the cutting teeth in one of the rows are staggered or offset from the tips of the cutting teeth in the other row, such that the tips of the cutting teeth in the one row are not aligned with the tips of the cutting teeth in the other row in a lateral direction perpendicular to a central longitudinal axis of the inner member. The first and second cutting edges on the outer member may be straight or non-toothed cutting edges, or may be toothed cutting edges as explained above for the first mentioned aspect of the invention.

A still further aspect of the present invention involves a rotary surgical instrument comprising an elongate tubular inner member in accordance with any of the aspects of the invention described above, in combination with an elongate tubular outer member having a distal portion with an aperture circumscribed by a peripheral surface having a narrow width portion forming a sharp cutting surface or edge along opposite sides of the aperture. The peripheral surface of the outer member has an inner peripheral edge adjoining an internal surface of the outer member and has an outer peripheral edge extending entirely around the inner peripheral edge in spaced relation therewith. The width of the narrow width portion of the peripheral surface is defined between the inner and outer peripheral edges. The outer member includes a beveled surface extending angularly outwardly from the outer peripheral edge to a border edge of the beveled surface adjoining the external surface of the outer member. The width of the peripheral surface along the narrow width portion thereof does not extend the full distance between the internal and external surfaces of the outer member such that the cutting surface or edge is thinner and of enhanced sharpness for greater cutting effectiveness in combination with the inner member of any of the above-described aspects of the invention.

Various objects, advantages and benefits of the present invention will become apparent from the following description of the preferred embodiments taken in conjunction with the accompanying drawings, wherein like parts in each of the several figures are identified by the same reference numerals or by reference numerals having the same last two digits.

BRIEF DESCRIPTION OF THE DRAWINGS

FIG. 13 is a broken perspective view of a distal portion of an outer member of the rotary surgical instrument of FIG. 12.

FIG. 14 is a top view of the distal portion of FIG. 13.

FIG. 15 is a distal end view of the distal portion of FIG. 13.

FIG. 16 is a fragmentary sectional view taken along line 16-16 of FIG. 13.

DESCRIPTION OF THE PREFERRED EMBODIMENTS

Figure 1:
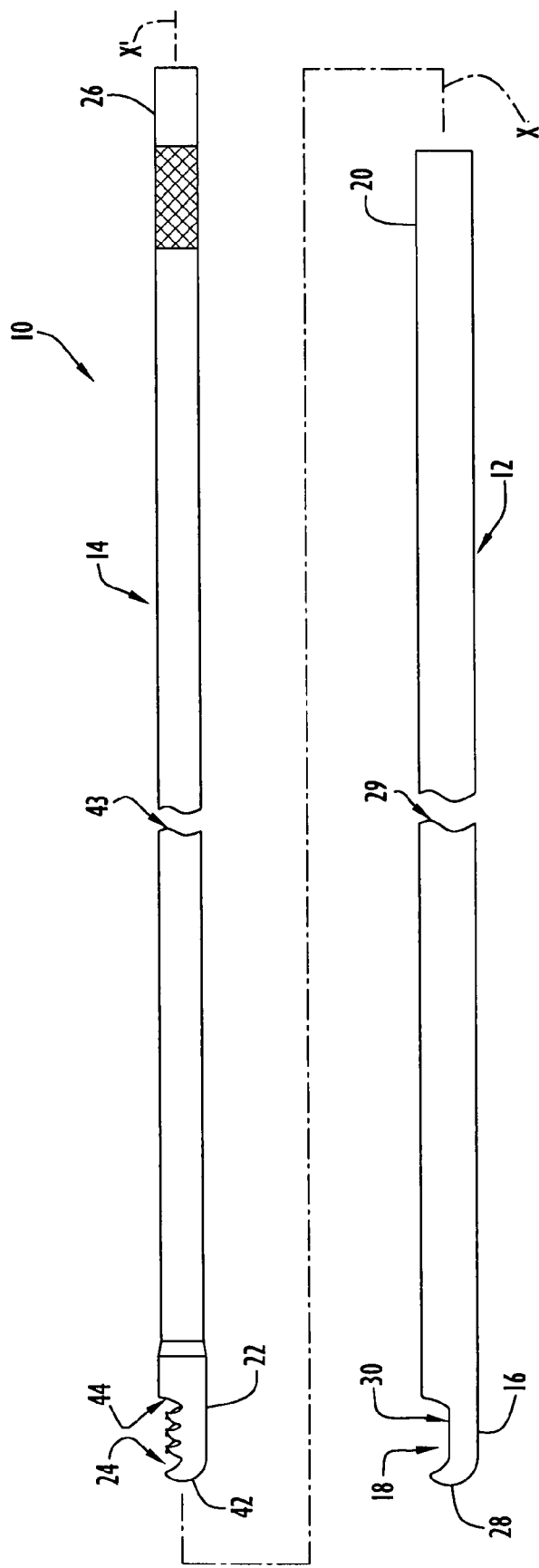
FIG. 1 is an exploded, broken side view of a rotary surgical instrument.
Figure 2:
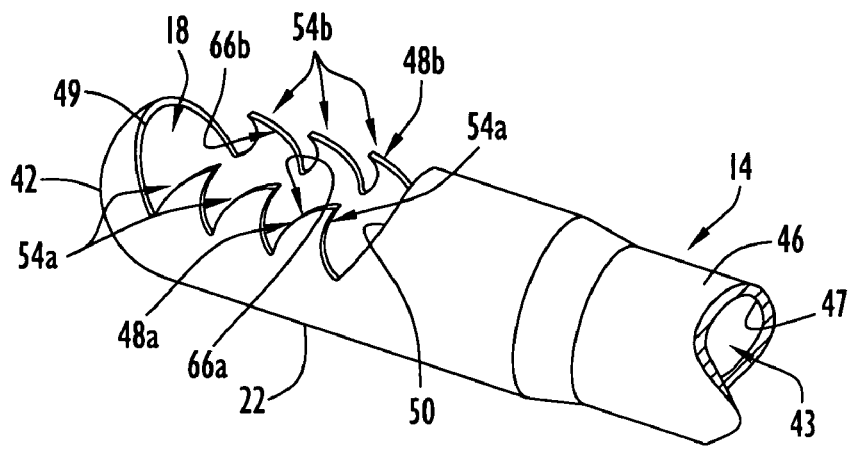
FIG. 2 is a broken perspective view of a distal portion of an inner member of the rotary surgical instrument.
Figure 3:
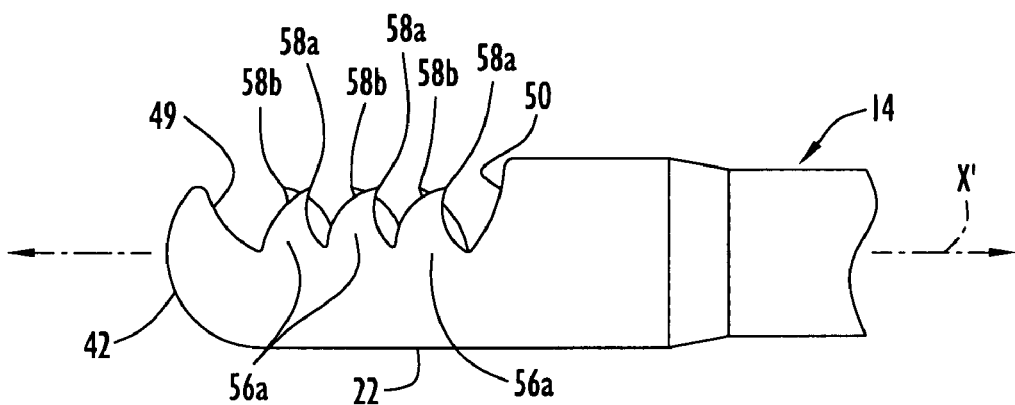
FIG. 3 is a broken side view of the distal portion of the inner member.
Figure 5:
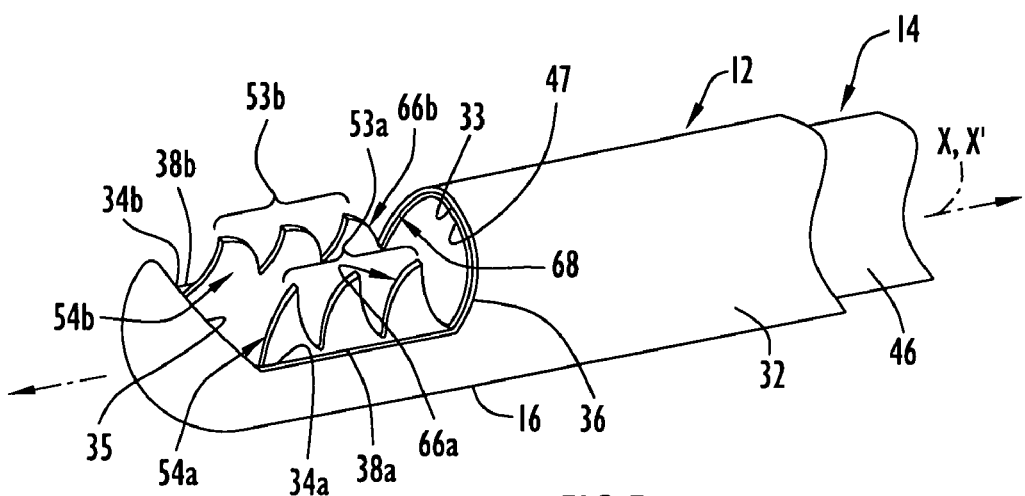
FIG. 5 is a broken perspective view of a distal portion of an outer member of the rotary surgical instrument with the inner member rotatably disposed within the outer member.

A rotary surgical instrument 10 is illustrated in FIGS. 1 and 5 and includes an elongate tubular outer member 12 and an elongate tubular inner member 14 for being rotatably disposed within the outer member 12. The outer member 12 is depicted in FIGS. 1 and 5 and has a central longitudinal axis X, a distal portion 16 with a cutting window or aperture 18, and a proximal end 20 for being coupled to a conventional powered surgical handpiece (not shown). The proximal end 20 of the outer member 12 can be coupled to the powered surgical handpiece in any suitable manner. The proximal end 20 can be attached to a conventional outer member hub (not shown) by which the outer member 12 is coupled to the handpiece, the outer member typically being coupled to the handpiece in fixed or stationary relation. The inner member 14 has a central longitudinal axis X', a distal portion 22 with a cutting window or aperture 24, and a proximal end 26 for being coupled with a motor of the powered surgical handpiece. The proximal end 26 of the inner member 14 can be coupled to the powered surgical handpiece in any suitable manner to be rotated by the motor unidirectionally or bidirectionally. The proximal end 26 can be attached to a conventional inner member hub (not shown) by which the inner member 14 is coupled to a drive shaft of the motor of the powered surgical handpiece for being rotated relative to and within the outer member 12. The outer member 12 and the inner member 14 can be removably coupled with the powered surgical handpiece, and it is conventionally known to design the outer and inner member hubs of rotary surgical instruments to be removably coupled to powered surgical handpieces. Accordingly, the rotary surgical instrument 10 can be removed from the powered surgical handpiece for disposal of the rotary surgical instrument 10 after use on a single patient while allowing re-use of the powered surgical handpiece. U.S. Pat. No. 6,533,749 discloses outer and inner member hubs for connection to a powered surgical handpiece as described in U.S. Pat. No. 5,916,231. To the extent necessary for a general understanding of representative outer and inner member hubs and a representative powered surgical handpiece for the rotary surgical instruments described herein, the disclosures of U.S. Pat. No. 6,533,749 and U.S. Pat. No. 5,916,231 are incorporated herein by reference.

The distal portion 16 of outer member 12 has a distal end formed by a distal end wall 28. The distal end wall 28 may be rounded and can have a convex or partial spherical configuration. The distal end wall 28 may have a configuration to form a closed or partly closed distal end for the outer member, as is the case for the outer member 12. The distal end wall 28 may extend to a height well above the central longitudinal axis X as is depicted for distal end wall 28. The distal end wall 28 could extend to a height aligned or nearly aligned with the central longitudinal axis X as described below for distal end wall 428. The aperture 18, which provides communication with the internal lumen 29 of the outer member 12, is a lateral or side-facing aperture formed in the distal portion 16 at, adjacent or close to the distal end of the outer member. The aperture 18 is circumscribed, bounded or bordered by a peripheral surface 30 extending entirely around the aperture 18 and defining the perimeter of the aperture 18. The peripheral surface 30 is disposed between the outer or external surface 32 of the outer member 12 and the inner or internal surface 33 of the outer member 12.

The peripheral surface 30 can be formed in the outer member 12 to define various perimeter configurations for aperture 18. The peripheral surface 30 for outer member 12 includes two side segments 34a and 34b respectively extending longitudinally along the outer member 12 on opposite sides of the central longitudinal axis X, a forward segment 35 distally joining the side segment 34a to the side segment 34b, and a rearward segment 36 proximally joining the side segment 34a to the side segment 34b to define the perimeter configuration for aperture 18. The side segments 34a and 34b form opposite sides of the aperture 18, and the forward and rearward segments 35 and 36 form opposite ends of the aperture 18. The side segments 34a and 34b may extend longitudinally along the outer member 12 in a longitudinally straight path, and may extend longitudinally in parallel with the central longitudinal axis X as is the case for outer member 12. However, it should be appreciated that the side segments 34a and 34b could extend longitudinally in a curved path and that the side segments 34a and 34b do not have to be parallel to the central longitudinal axis X. The forward segment 35 extends between the side segments 34a and 34b transverse to the central longitudinal axis X and forms a closed forward end for the aperture 18. The forward segment 35 can extend in an arcuate or curved path between the side segments 34a and 34b. The rearward segment 36 extends between the side segments 34a and 34b transverse to the central longitudinal axis X and forms a closed rearward end for the aperture 18. The rearward segment 36 can extend in an arcuate or curved path between the side segments 34a and 34b. As seen in FIGS. 1 and 5, the forward segment 35 is angled in the distal direction from the side segments 34a, 34b, and the rearward segment 36 is angled in the proximal direction from the side segments 34a, 34b. The perimeter configuration for aperture 18 may be symmetrical with respect to the central longitudinal axis X as is the case for outer member 12.

The outer member 12 includes a cutting element on its distal portion 16 comprising two sharp cutting edges 38a and 38b of peripheral surface 30 extending respectively along the side segments 34a and 34b. The cutting edges 38a and 38b may be formed in the outer member 12 in any suitable manner including conventionally in the manner of a "full radius" design. The side segments 34a, 34b of peripheral surface 30 may be formed to extend angularly between the external surface 32 and the internal surface 33 of the outer member 12 at an acute angle to form the cutting edges 38a, 38b along the side segments 34a, 34b. The cutting edges 38a, 38b follow the longitudinal path of the respective side segments 34a, 34b. In the case of outer member 12, the cutting edges 38a, 38b are straight cutting edges, i.e. cutting edges without a toothed configuration, respectively disposed on opposite sides of the aperture 18 and central longitudinal axis X, and the cutting edges 38a,38b extend parallel to the central longitudinal axis X. Although the straight or non-toothed cutting edges 38a, 38b are depicted as following a longitudinally straight path, the straight or non-toothed cutting edges 38a,38b can follow a longitudinally curved path. The cutting element of the outer member 12 may extend or continue along the forward segment 35 of the peripheral surface 30.

The distal portion 22 of inner member 14 has a distal end formed by a distal end wall 42. The distal end wall 42 may be rounded and can have a convex or partial spherical configuration. The distal end wall 42 may have a configuration to form a closed or partly closed distal end for the inner member, as is the case for the inner member 14. The distal end wall 42 may extend to a height that is equivalent to the height of the outer member distal end wall 28 and may fit in a complementary manner with the outer member distal end wall when the inner member 14 is assembled with the outer member 12 to form the instrument 10. The aperture 24, which provides communication with the internal lumen 43 of the inner member 14, is a lateral or side-facing aperture formed in a thin-walled, hollow or tubular part of the distal portion 22 at, adjacent or close to the distal end of the inner member. The aperture 24 is circumscribed, bounded or bordered by a peripheral surface 44 extending entirely around the aperture 24 and defining the perimeter of the aperture 24. The peripheral surface 44 is disposed between the outer or external surface 46 of the inner member 14 and the inner or internal surface 47 of the inner member 14.

The peripheral surface 44 can be formed in the inner member 14 to define various perimeter configurations for aperture 24. The aperture 24 can be formed with a perimeter configuration that is the same as or similar to the perimeter configuration of the outer member aperture 18 as is depicted for instrument 10. The peripheral surface 44 for inner member 14 includes two side segments 48a and 48b respectively extending longitudinally along the inner member 14 on opposite sides of the central longitudinal axis X', a forward segment 49 distally joining the side segment 48a to the side segment 48b, and a rearward segment 50 proximally joining the side segment 48a to the side segment 48b to define the perimeter configuration for aperture 24. The side segments 48a and 48b form opposite sides of the aperture 24, and the forward and rearward segments 49 and 50 form opposite ends of the aperture 24. The side segments 48a and 48b may extend longitudinally along the inner member 14 in a longitudinally straight path, and may extend longitudinally in parallel to its central longitudinal axis X' as is the case for inner member 14. However, it should be appreciated that the side segments 48a and 48b could extend longitudinally in a curved path and that the side segments 48a and 48b do not have to be parallel to the central longitudinal axis X'. As explained further below, the side segments 48a and 48b are each configured to form the distal (forward) and proximal (rearward) sides of a series of cutting teeth comprising the cutting element of the inner member 14. The forward segment 49 extends between the side segments 48a and 48b transverse to the central longitudinal axis X' and forms a closed forward end for the aperture 24. The forward segment 49 can extend in an arcuate or curved path between the side segments 48a and 48b. The rearward segment 50 extends between the side segments 48a and 48b transverse to the central longitudinal axis X' and forms a closed rearward end for the aperture 24. The rearward segment 50 can extend in an arcuate or curved path between the side segments 48a and 48b. As seen in FIGS. 1-4, the forward segment 49 may be angled in the distal direction from the side segments 48a, 48b, and the rearward segment 50 may be angled in the proximal direction from the side segments 48a, 48b. The perimeter configuration for aperture 24 may be symmetrical with respect to the central longitudinal axis X' as is the case for inner member 14.

The inner member 14 includes a cutting element on its distal portion 22, the inner member cutting element comprising a first row 53a of cutting teeth 54a and a second row 53b of cutting teeth 54b respectively disposed on opposite sides of the aperture 24 and central longitudinal axis X'. As explained further below, the side segment 48a of peripheral surface 44 has a configuration to form distal (forward) and proximal (rearward) sides of the cutting teeth 54a, and the side segment 48b of peripheral surface 44 has a configuration to form distal (forward) and proximal (rearward) sides of the cutting teeth 54b. Row 53a includes a plurality or series of cutting teeth 54a, and row 53b includes a plurality or series of cutting teeth 54b. The same number of cutting teeth may be provided in each row 53a and 53b. As an example, row 53a is shown with three cutting teeth 54a, and row 53b is shown with three cutting teeth 54b. It should be appreciated, however, that any suitable number of one or more cutting teeth can be provided as the series of cutting teeth in each row 53a and 53b, and that the number of cutting teeth in row 53a can be different from the number of cutting teeth in row 53b. The rows 53a, 53b of cutting teeth 54a, 54b follow the longitudinal path of the respective side segments 48a, 48b. In the case of inner member 14, the rows 53a and 53b of cutting teeth extend linearly in a straight longitudinal path, and the cutting teeth of each row 53a, 53b are arranged in a straight line. The rows 53a and 53b of cutting teeth may extend longitudinally in parallel with the central longitudinal axis X' as is depicted for inner member 14. As described in greater detail below, the inner member cutting element comprising the rows 53a and 53b of cutting teeth 54a and 54b cooperates with the cutting edges 38a and 38b of the outer member cutting element to cut anatomical tissue positioned in the outer member aperture 18 as the inner member cutting element rotates past the outer member aperture 18. As explained further below, each cutting tooth 54a, 54b has a convexly curved side and, therefore, is convexly curved. The cutting teeth 54a in row 53a are all convexly curved in the same direction. The cutting teeth 54b in row 53b are all convexly curved in the same direction, but the direction of convex curvature for cutting teeth 54b is opposite the direction of convex curvature for cutting teeth 54a.

Figure 4:
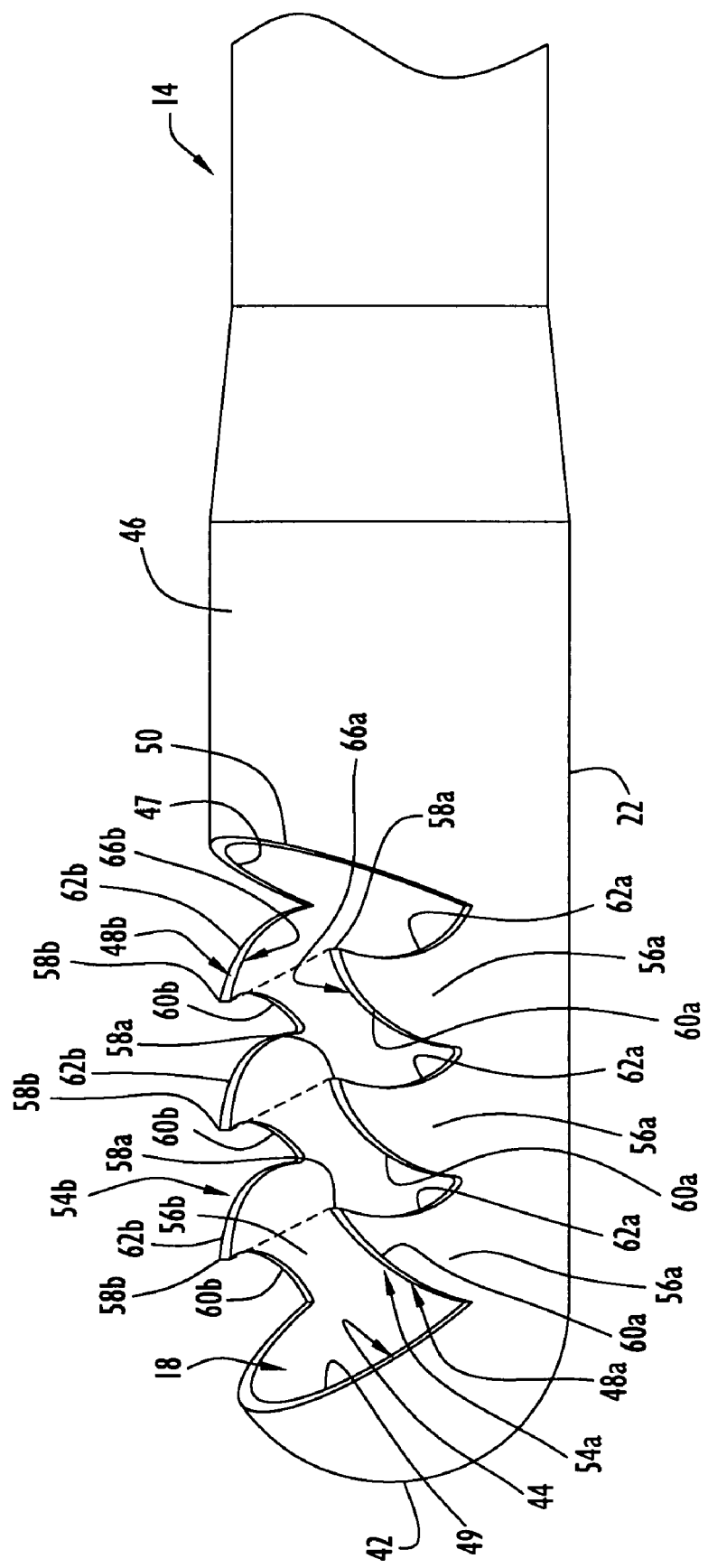
FIG. 4 is an enlarged, broken, side perspective view of the distal portion of the inner member.

As best seen in FIG. 4, each cutting tooth 54a includes a base or root 56a, a tip 58a, a convex side 60a extending from the root 56a to the tip 58a with a convex curvature in the proximal direction, and an opposed side 62a extending from the root 56a to the tip 58a. Each cutting tooth 54a also has an outer or external face formed by the external surface 46 of the inner member 14 and has an inner or internal face formed by the internal surface 47 of the inner member 14. In the case of cutting teeth 54a, the convex sides 60a are distal or forward sides of the cutting teeth, and the opposed sides 62a are proximal or rearward sides of the cutting teeth. The forward and rearward sides 60a and 62a of cutting teeth 54a are formed by the side segment 48a of the peripheral surface 44 of the inner member aperture 24.

The forward and rearward sides 60a and 62a of each cutting tooth 54a meet at the tip 58a of the cutting tooth to form a sharp point. The forward and rearward sides 60a and 62a of each cutting tooth 54a define its geometric profile. In the case of cutting teeth 54a, the rearward sides 62a are also convexly curved but could be formed without a convex curvature. The rearward sides 62a of the cutting teeth 54a extend from the root 56a to the tip 58a of the cutting tooth with a convex curvature in the same direction as the forward side 60a. Accordingly, the rearward sides 62a curve convexly in the proximal direction from the roots 56a to the tips 58a such that the cutting teeth 54a have a partial crescent-shaped geometric profile curving convexly in the proximal direction. As depicted for cutting teeth 54a, the forward sides 60a may have a more gradual curvature than the rearward sides 62a. Also, the forward side 60a of each cutting tooth 54a may curve over the rearward side 62a so that the geometric profile is somewhat hook-shaped. The geometric profile for the cutting teeth 54a retains a greater quantity of material or mass in the inner member 14 than typical triangular geometric profiles or geometric profiles composed of concave sides, and more mass is retained above the central longitudinal axis X'.

The root 56a of each cutting tooth 54a is connected to the root of the next adjacent cutting tooth 54a in the row 53a. In particular, except for the distalmost cutting tooth 54a, the forward side 60a of each cutting tooth 54a is joined to the rearward side 62a of the next adjacent distal cutting tooth 54a at their roots 56a. The distalmost cutting tooth 54a has its forward side 60a joined at its root 56a to the forward segment 49 of the peripheral surface 44 of the inner member aperture 24. Conversely, except for the proximalmost cutting tooth 54a, the rearward side 62a of each cutting tooth 54a is joined to the forward side 60a of the next adjacent proximal cutting tooth 54a at their roots 56a. The proximalmost cutting tooth 54a has its rearward side 62a joined at its root 56a to the rearward segment 50 of the peripheral surface 44 of the inner member aperture 24.

The cutting teeth 54b of row 53b have the same convexly curved geometric profile as the cutting teeth 54a but are convexly curved in the distal direction, opposite the direction of convex curvature for the cutting teeth 54a. Each cutting tooth 54b has a base or root 56b, a tip 58b, a convex side 62b extending from the root 56b to the tip 58b with a convex curvature in the distal direction, and an opposed side 60b extending from the root 56b to the tip 58b. The sides 62b are proximal or rearward sides of the cutting teeth 54b, and the sides 60b are distal or forward sides of the cutting teeth 54b. The cutting teeth 54b have a partial crescent-shaped geometric profile defined by the forward and rearward sides 60b and 62b that is the same as the geometric profile of cutting teeth 54a but with a convex curvature in the distal direction. Each cutting tooth 54b also has an outer or external face formed by the external surface 46 of the inner member 14 and has an inner or internal face formed by the internal surface 47 of the inner member 14. The forward and rearward sides 60b and 62b of cutting teeth 54b are formed by side segment 48b of the peripheral surface 44 of the inner member aperture 24.

The forward side 60b of each cutting tooth 54b is like the rearward sides 62a of cutting teeth 54a except that the forward sides 60b curve in a direction opposite the direction of curvature for rearward sides 62a. Accordingly, the forward side 60b of each cutting tooth 54b extends from the root 56b to the tip 58b of the cutting tooth with a convex curvature in the distal direction. The rearward side 62b of each cutting tooth 54b is like the forward sides 60a of cutting teeth 54a except that the rearward sides 62b curve convexly in the distal direction opposite the direction of convex curvature for forward sides 60a. The forward and rearward sides 60b and 62b of each cutting tooth 54b meet at the tip 58b of the cutting tooth to form a sharp point and define the same partial crescent-shaped geometric profile as the teeth 54a but curving convexly in the distal direction. Of course, it should be appreciated that the direction of convex curvature for the cutting teeth 54a, 54b can be reversed in that the cutting teeth 54a can be convexly curved in the distal direction and the cutting teeth 54b can be convexly curved in the proximal direction.

The root 56b of each cutting tooth 54b is connected to the root of the next adjacent cutting tooth 54b in the row 53b. Except for the distalmost cutting tooth 54b, the forward side 60b of each cutting tooth 54b is joined to the rearward side 62b of the next adjacent distal cutting tooth 54b at their roots 56b. The distalmost cutting tooth 54b has its forward side 60b joined at its root 56b to the forward segment 49 of the peripheral surface 44 of the inner member aperture 24. Conversely, except for the proximalmost cutting tooth 54b, the rearward side 62b of each cutting tooth 54b is joined to the forward side 60b of the next adjacent proximal cutting tooth 54b at their roots 56b. The proximalmost cutting tooth 54b has its rearward side 62b joined at its root 56b to the rearward segment 50 of the peripheral surface 44.

The cutting teeth 54a, 54b are preferably formed in the inner member 14 by normal laser cutting of the thin-walled, hollow or tubular part of the distal portion 22. The cutting teeth 54a, 54b may be formed in the inner member 14 in conjunction with laser cutting the aperture 24 in the thin-walled, hollow or tubular part of distal portion 22, resulting in formation of the peripheral surface 44 and the cutting teeth 54a and 54b. The side segments 48a, 48b of peripheral surface 44 that result from laser cutting the inner member 14 form sharp cutting edges 66a and 66b, or knife edges, along the respective side segments 48a and 48b of sufficient sharpness to sheer cut anatomical tissue. Preferably, the thin-walled, hollow or tubular part of distal portion 22 has a wall thickness between its external surface 46 and its internal surface 47 in the range of 0.008 to 0.0015 of an inch to obtain the knife-sharp cutting edges as a direct result of laser cutting the thin-walled, hollow or tubular part in the configuration of the cutting teeth 54a, 54b.

The cutting edge 66a extends along the entire length of the forward sides 60a of the cutting teeth 54a from the roots 56a to the sharp points at the tips 58a of the cutting teeth. The cutting edge 66a can also extend along the rearward sides 62a of the cutting teeth 54a. In the case of cutting teeth 54a, the cutting edge 66a extends along the entire or substantially the entire length of the rearward sides 62a between the roots 56a and the tips 58a of the cutting teeth. The cutting teeth 54a allow the length of the forward sides 60a to be maximally utilized for shear cutting anatomical tissue, and allow the geometric profile of the cutting teeth to be maximally utilized to shear anatomical tissue. The cutting edge 66b extends along the entire length of the rearward sides 62b of the cutting teeth 54b from the roots 56b to the sharp points at the tips 58b, allowing the length of the rearward sides 62b to be maximally utilized for shear cutting anatomical tissue. The cutting edge 66b also extends along the entire or substantially the entire length of the forward sides 60b, and the geometric profile of the cutting teeth 54b can be maximally utilized to shear anatomical tissue. Of course, it should be appreciated that the cutting edges 66a, 66b could extend or continue along all or part of the forward segment 49 and/or the rearward segment 50 of the peripheral surface 44, and that the cutting edges 66a, 66b can be part of a continuous sharp edge extending entirely or substantially entirely around the aperture 24 along the peripheral surface 44.

Each cutting tooth 54a has a width at its root 56a, and all of the cutting teeth 54a in row 53a are of the same or uniform width. All of the cutting teeth 54b in row 53b have the same width as the cutting teeth 54a. Each cutting tooth 54a has a height between its root 56a and the highest point of the arc of its side 60a. Each cutting tooth 54b has a height between its root 56b and the highest point of the arc of its side 62b. All of the cutting teeth 54a in row 53a are of the same or uniform height. The cutting teeth 54b in row 53b have the same height as the cutting teeth 54a. The tips 58a of cutting teeth 54a are uniformly longitudinally spaced from one another in row 53a. The tips 58b of cutting teeth 54b are uniformly longitudinally spaced from one another in row 53b with the same longitudinal spacing as the cutting teeth 54a, but the tips 58b are staggered or offset with respect to the tips 58a in a lateral direction across aperture 24 as best shown in FIG. 4. Accordingly, the tips 58a of the cutting teeth 54a are not in alignment with the tips 58b of the corresponding cutting teeth 54b in a lateral direction perpendicular to the central longitudinal axis X' of the inner member 14. Rather, the tips 58a of the cutting teeth 54a are situated obliquely, diagonally or non-perpendicularly to the tips 58b of the corresponding cutting teeth 54b in the lateral direction across aperture 24 as shown by the oblique or diagonal dotted lines in FIG. 4.

As shown in FIG. 5, the rotary surgical instrument 10 is assembled with the inner member 14 rotatably disposed within the internal lumen 29 of the outer member 12. The proximal end 26 of the inner member 14 is coupled with the drive shaft of a motor of a powered surgical handpiece for rotating the inner member 14. The proximal end 20 of the outer member 12 is coupled with the handpiece in fixed or stationary relation so that the inner member 14 can be rotated relative to and within the internal lumen 29 of the outer member 12. Although the inner member 14 will most typically be rotated unidirectionally in one direction, i.e. clockwise or counterclockwise, within the outer member 12, it should be appreciated that the inner member 14 can be rotated bidirectionally or oscillated within the outer member 12. The handpiece mounts the inner member 14 for rotation coaxially within the outer member 12, and the outer surface of the distal end wall 42 of the inner member can be in bearing relation or contact with the inner surface of the outer member distal end wall 28 to assist in maintaining coaxial alignment of the outer and inner members. The rows 53a, 53b of cutting teeth 54a, 54b comprising the cutting element of the inner member 14 are in alignment with the aperture 18 in the outer member 12. As the inner member 14 is rotated relative to and within the outer member 12, the cutting teeth 54a, 54b repetitively move or rotate past the outer member aperture 18. Accordingly, the cutting teeth 54a, 54b and the cutting edges 66a, 66b of the cutting teeth 54a, 54b cooperate with the cutting edges 38a, 38b of the outer member to cut anatomical tissue positioned in the aperture 18.

In use during a surgical procedure on a patient, the instrument 10 will normally be introduced through an incision or portal to position the distal portion of the instrument at an operative site in the patient's body with the outer member 12 extending through the portal or incision so that the powered surgical handpiece remains external of the patient's body. The instrument 10 is manipulated to position the aligned apertures 18, 24 to receive anatomical tissue intended to be cut as part of the surgical procedure. The inner member 14 is rotated within the outer member 12 to move the cutting teeth 54a, 54b past the edges 38a, 38b to cut the anatomical tissue.

Since the knife-sharp cutting edges 66a, 66b extend along the entire length of the respective sides 60a, 62b, shear cutting of the anatomical tissue can occur along the entire length of these sides in the upper or tip regions of the cutting teeth 54a, 54b and in the lower or root regions of the cutting teeth 54a, 54b. Shear cutting of the tissue can also occur along the sides 62a, 60b of the cutting teeth 54a, 54b due to the presence of the knife-sharp cutting edges 66a, 66b along these sides. With the cutting teeth 54a, 54b, shear cutting can occur along the sides 62a, 60b in the tip regions and the root regions of the cutting teeth. The cutting teeth 54a, 54b allow shear cutting of the anatomical tissue to occur over an increased area and over a greater proportion of the geometrical profile of the teeth. The shear cutting action of the cutting teeth 54a, 54b is more uniform and continuous because it takes place along the upper or tip regions of the cutting teeth 54a, 54b as well as the lower or root regions of the cutting teeth where squeezing and tearing of the tissue is avoided. Anatomical tissue is thusly cut more cleanly and with less trauma. Torque is also distributed by the cutting teeth 54a, 54b with increased uniformity and continuity, and the torque and force required to cut anatomical tissue is reduced. The cutting teeth 54a, 54b, including the tips 58a, 58b, are of greater rigidity and strength due to their geometric profile and due to there being no fragile tips or points on the cutting teeth. The tips 58a, 58b of the cutting teeth 54a, 54b are pointed to facilitate penetration of the anatomical tissue but are not weak and fragile. The total tooth area has adequate strength and rigidity, thereby reducing the potential for deformation, breakage, bending and distortion. The convexly curved design for the cutting teeth 54a, 54b enables all of the teeth in a row to cut uniformly with a constant torque load distributed over a greater closing area as the outer member aperture 18 is "closed" by the inner member 14 when the teeth move past the cutting edges 38a, 38b. The convexly curved design of the cutting teeth 54a, 54b also minimizes the possibility of distortion arising from hoop stress within the tubular inner member. Bearing contact or relation between the outer and inner members 12 and 14 is improved and the bearing area is maximized due to there being more mass or material retained in the inner member 14 above its central longitudinal axis X'. Each row 53a, 53b of cutting teeth 54a, 54b provides a different shear cutting action or effect due to the cutting teeth 54a being convexly curved in the opposite direction from the cutting teeth 54b and due to the tips 58a being staggered with respect to the tips 58b. Accordingly, the shear cutting action or effect provided by the row 53a of cutting teeth 54a is not duplicative of the shear cutting action or effect provided by the row 53b of cutting teeth 54b. Anatomical tissue is thusly cut with greater aggressiveness and efficiency, and the anatomical tissue can be cut more quickly which reduces the time needed to complete the surgical procedure.

The internal lumen 43 of the inner member 14 may be connected with a source of vacuum or suction to serve as an aspiration passage for fluids and anatomical tissue. Anatomical tissue cut by the instrument 10 is drawn into the internal lumen 43 and is removed through the instrument. As shown in FIG. 5, the aperture 24 in the inner member 14 repetitively comes into rotational alignment with the outer member aperture 18 as the inner member 14 rotates within the outer member 12. When the apertures 18 and 24 are rotationally aligned, suction from the internal lumen 43 of the inner member is applied at the operative site to remove fluids and/or anatomical tissue. An annular gap or clearance 68 between the internal surface 33 of the outer member 12 and the external surface 46 of the inner member 14 may be connected with a supply of irrigation fluid to serve as an irrigation passage from which irrigation fluid is supplied to the operative site via the aperture 18. The radial dimension of the annular gap 68 can be minimized due to the increased resistance of the inner member 14 to bending, deformation and distortion. Since the radial dimension of the annular gap 68 can be minimized, the external diameter of the outer member 12 can be minimized which reduces the size of the portal or incision needed for introduction of the instrument at the operative site.

Figure 6:
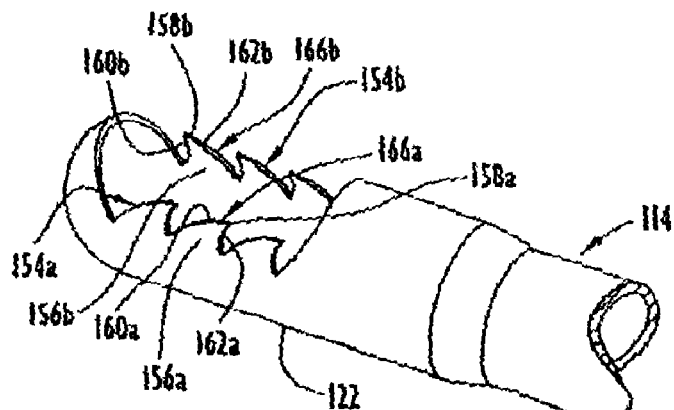
FIG. 6 is a broken perspective view of a distal portion of an alternative inner member for a rotary surgical instrument.
Figure 7:
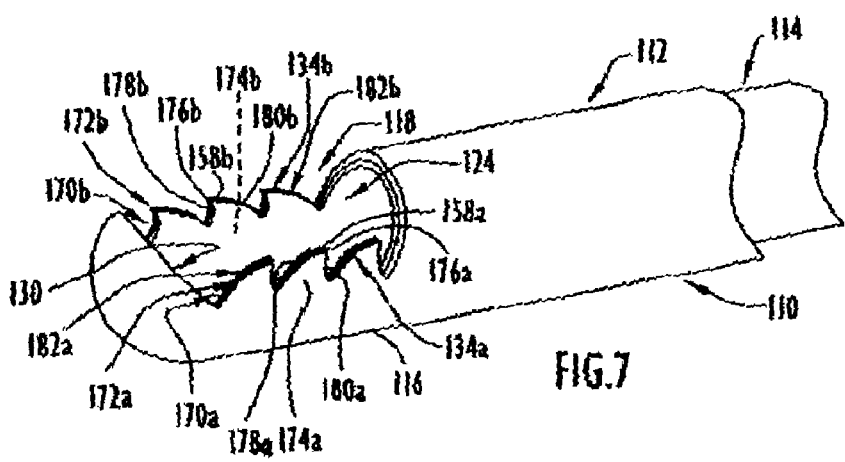
FIG. 7 is a broken perspective view of a distal portion of an alternative outer member with the alternative inner member rotatably disposed therein to form an alternative rotary surgical instrument.

FIG. 6 depicts the distal portion 122 of an alternative inner member 114 for a rotary surgical instrument. FIG. 7 depicts the distal portion of an alternative rotary surgical instrument 110 comprising inner member 114 assembled with an alternative outer member 112. The inner member 114 is similar to inner member 14 except that the convex curvature for the cutting teeth 154a and 154b comprising the cutting element of the inner member 114 is different from the convex curvature of the cutting teeth 54a and 54b. Also, the cutting teeth 154a and 154b are greater in width and smaller in height than the cutting teeth 54a and 54b. The convex sides 160a, 162b of the cutting teeth 154a, 154b are not as steep as the convex sides 60a, 62b of the cutting teeth 54a, 54b. The sides 162a, 160b of the cutting teeth 154a, 154b are similar to the sides 62a, 60b of the cutting teeth 54a, 54b in that they are convexly curved in the same direction as their corresponding sides 160a, 162b. The cutting edges 166a, 166b of the inner member cutting element are like the cutting edges 66a, 66b. The cutting edge 166a extends entirely along the forward sides 160a from the roots 156a to the tips 158a of the respective teeth 154a. The cutting edge 166a extends entirely or substantially entirely along the rearward sides 162a between the roots 156a and the tips 158a of the respective teeth 154a. The cutting edge 166b extends entirely along the rearward sides 162b from the roots 156b to the tips 158b and extends entirely or substantially entirely along the forward sides 160b between the roots 156b and the tips 158b of the respective cutting teeth 154b.

The outer member 112 has a different cutting element than the cutting element of the outer member 12, the cutting element of outer member 112 being essentially the same as the cutting element for the inner member 114. The cutting element for outer member 112 comprises a first row 170a of a series or plurality of cutting teeth 172a on one side of the outer member aperture 118 and a second row 170b of a series or plurality of cutting teeth 172b on the opposite side of the outer member aperture 118. The cutting teeth 172a are formed by the side segment 134a of the peripheral surface 130 of the outer member aperture 118, and the cutting teeth 172b are formed by the side segment 134b of the peripheral surface 130 of the outer member aperture 118. The cutting teeth 172a of row 170a are like the cutting teeth 154a of the inner member cutting element. Each cutting tooth 172a has a base or root 174a, a tip 176a, a distal or forward side 178a extending from the root 174a to the tip 176a with a convex curvature in the proximal direction, and a proximal or rearward side 180a extending from the root 174a to the tip 176a. The rearward sides 180a are like the rearward sides 162a of cutting teeth 154a and are convexly curved in the proximal direction from the root 174a to the tip 176a of the cutting tooth 154a. The forward and rearward sides 178a and 180a define the geometric profile for each cutting tooth 172a, which is the same as the geometric profile of the cutting teeth 154a on the inner member 114.

The cutting teeth 172b of row 170b have the same geometric profile as the cutting teeth 172a but have a convex curvature in the distal direction opposite the direction of convex curvature of cutting teeth 172a. The cutting teeth 172b are like the cutting teeth 154b of the inner member cutting element. Each cutting tooth 172b has a root 174b, a tip 176b, a forward side 178b extending from the root 174b to the tip 176b, and a rearward side 180b extending from the root 174b to the tip 176b with a convex curvature in the distal direction. The forward sides 178b of cutting teeth 172b are like the rearward sides 180a of cutting teeth 172a but are convexly curved in the distal direction opposite the direction of convex curvature of the rearward sides 180a. The rearward sides 180b of cutting teeth 172b are like the forward sides 178a of the cutting teeth 172a but curve convexly in the distal direction opposite the direction of convex curvature of the forward sides 178a. Also, the cutting teeth 172b are staggered or offset in the lateral direction from the cutting teeth 172a by the same distance that the cutting teeth 154b are staggered or offset from the cutting teeth 154a. Accordingly, when the inner member 114 is rotatably disposed within the outer member 112 with their apertures 118, 124 in rotational alignment as shown in FIG. 7, the geometric profiles of the cutting teeth 172a are in matching overlapping alignment with the geometric profiles of the cutting teeth 154a, and the geometric profiles of the cutting teeth 172b are similarly in matching overlapping alignment with the geometric profiles of the cutting teeth 154b. The aligned tips 158a, 176a of cutting teeth 154a, 172a are staggered or offset in the lateral direction from the aligned tips 158b, 176b of cutting teeth 154b, 172b.

The cutting teeth 172a and 172b are preferably formed in a thin-walled, hollow or tubular part of the distal portion 116 of the outer member 112 by normal laser cutting as described above for inner member 14, resulting in knife-sharp cutting edges 182a and 182b respectively along the side segments 134a and 134b of the peripheral surface 130. The thin-walled, hollow or tubular part of distal portion 116 can have a wall thickness between its external surface and its internal surface in the same range as the wall thickness of distal portion 22 to obtain the knife sharp cutting edges as a direct result of laser cutting the thin-walled, hollow or tubular part to form the cutting teeth 172a, 172b. The cutting edge 182a extends entirely along the length of the forward sides 178a from the roots 174a to the tips 176a and extends entirely or substantially entirely along the length of the rearward sides 180a between the roots 174a and the tips 176a of the cutting teeth 172a as described above for the cutting edges 66a, 166a. The cutting edge 182b similarly extends entirely along the length of the rearward sides 180b from the roots 174b to the tips 176b and extends entirely or substantially entirely along the length of the forward sides 178b between the roots 174b and the tips 176b of the respective cutting teeth 172b as described above for the cutting edges 66b, 166b. As described above for the cutting edges 66a, 66b and 166a, 166b, the cutting edges 182a, 182b can extend or continue along all or part of the forward segment and/or the rearward segment of the peripheral surface 130, and the cutting edges 182a, 182b could be part of a single continuous cutting edge extending entirely or substantially entirely around the outer member aperture 118. The cutting edges 166a, 166b on the cutting teeth 154a, 154b of the inner member 114 cooperate with the cutting edges 182a, 182b on the outer member cutting teeth 172a, 172b to cut anatomical tissue within the outer member aperture 118 as the inner member 114 is rotated relative to and within the outer member 112 as described above for rotary surgical instrument 10. The outer member 112, the inner member 114 and the rotary surgical instrument 110 provide various advantages and benefits as described above for inner member 14 and instrument 10. Furthermore, the instrument 110 will generally provide a more aggressive cutting action than the instrument 10 due to the outer member 112 having a cutting element comprised of cutting teeth and non-straight cutting edges. It should be appreciated that the inner member 114 can be utilized in combination with the outer member 12 to form a different alternative rotary surgical instrument. It would also be possible for the outer member 112 to be used in combination with the inner member 14 to form a different alternative rotary surgical instrument.

Figure 8:
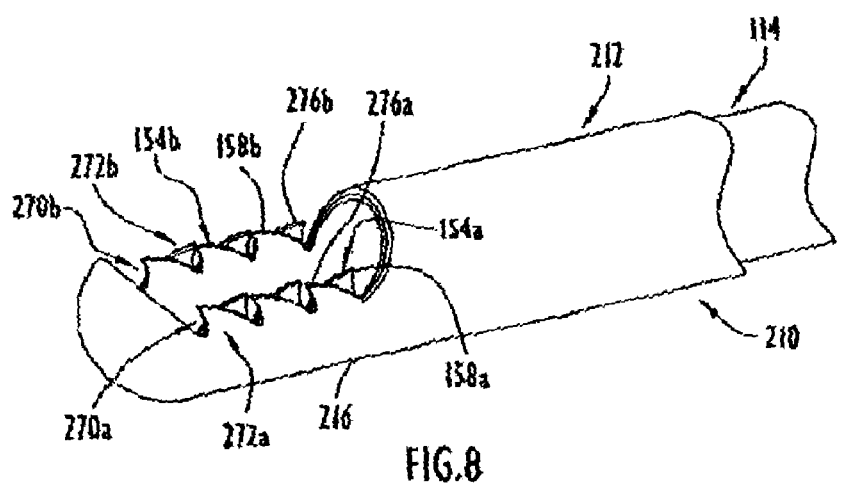
FIG. 8 is a broken perspective view of a distal portion of another alternative outer member with the inner member of FIG. 6 rotatably disposed therein to form another alternative rotary surgical instrument.

FIG. 8 illustrates a further alternative rotary surgical instrument 210 which is representative of an instrument wherein the first row of cutting teeth on the outer member have a convex curvature opposite the direction of convex curvature for the first row of cutting teeth on the inner member and, similarly, the second row of cutting teeth on the outer member have a convex curvature opposite the direction of convex curvature for the second row of cutting teeth on the inner member. The instrument 210 comprises the inner member 114 rotatably disposed in an outer member 212, which is like the outer member 112 except that the cutting teeth 272a in row 270a are like the cutting teeth 172b while the cutting teeth 272b in row 270b are like the cutting teeth 172a. Accordingly, the cutting teeth 272a are convexly curved in the distal direction while the cutting teeth 272b are convexly curved in the proximal direction. The cutting teeth 272a are therefore like the cutting teeth 154b of the inner member 114, and the cutting teeth 272b are like the inner member cutting teeth 154a. The tips 158a of the cutting teeth 154a are staggered or offset from the tips 276a of the corresponding cutting teeth 272a. Similarly, the tips 158b of the cutting teeth 154b are staggered or offset from the tips 276b of the corresponding cutting teeth 272b.

Figure 9:
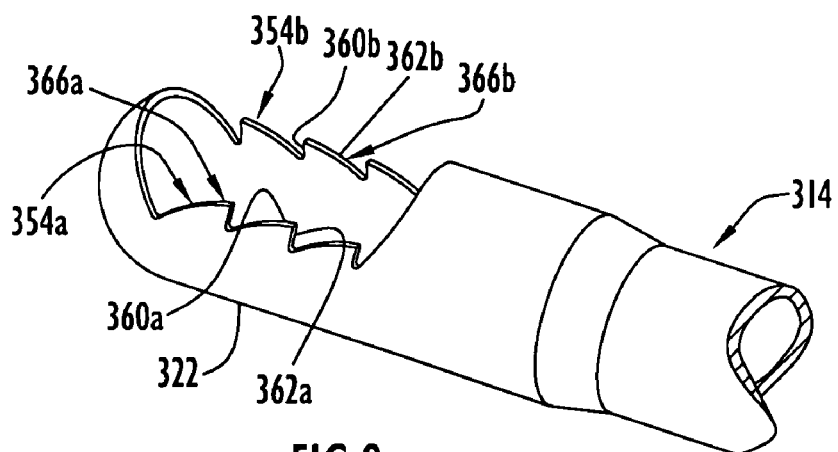
FIG. 9 is a broken perspective view of a distal portion of a further alternative inner member for a rotary surgical instrument.
Figure 10:
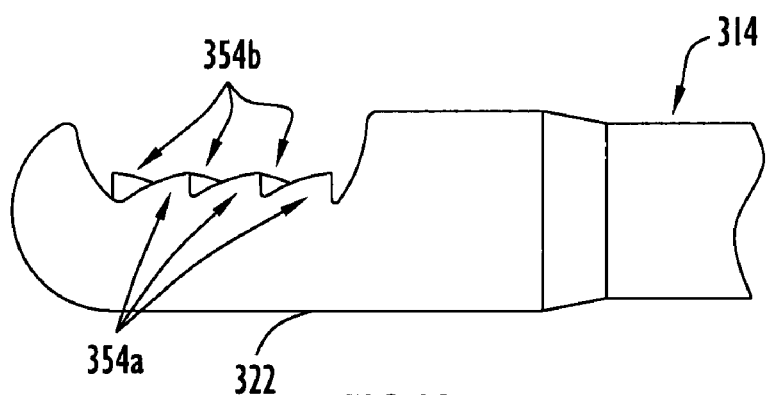
FIG. 10 is a broken side view of the distal portion of the further alternative inner member.
Figure 11:
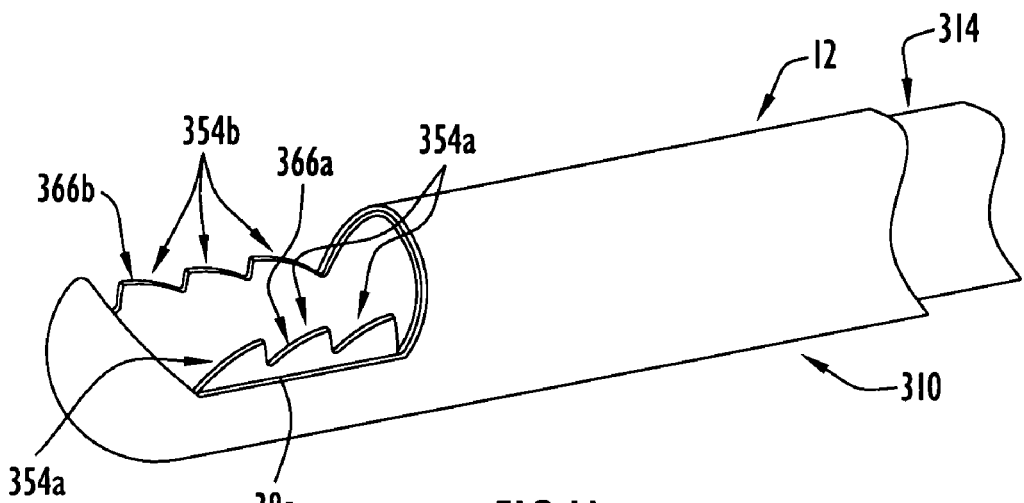
FIG. 11 is a broken perspective view of the distal portion of the outer member of FIGS. 1 and 5 with the further alternative inner member rotatably disposed therein to form a further alternative rotary surgical instrument.

Another alternative inner member for a rotary surgical instrument is depicted at 314 in FIGS. 9 and 10. FIG. 11 depicts the inner member 314 assembled with the outer member 12 to form an alternative rotary surgical instrument 310. The inner member 314 is similar to the inner members 14, 114 and 214 except that the forward sides 360a of cutting teeth 354a and the rearward sides 362b of the cutting teeth 354b have a more gradual convex curvature. In addition, the rearward sides 362a of cutting teeth 354a and the forward sides 360b of the cutting teeth 354b are straight and not curved. The cutting teeth 354a, 354b are formed in the thin-walled, hollow or tubular part of distal portion 322 of inner member 314 by normal laser cutting, which results in knife-sharp cutting edges 366a and 366b similar to the cutting edges 66a, 166a and 66b, 166b. Although the inner member 314 is depicted in FIG. 11 assembled with the outer member 12 to form the rotary surgical instrument 310, it should be appreciated that the inner member 314 can be combined with various outer members having straight or toothed cutting elements to form a rotary surgical instrument.

Figure 12:
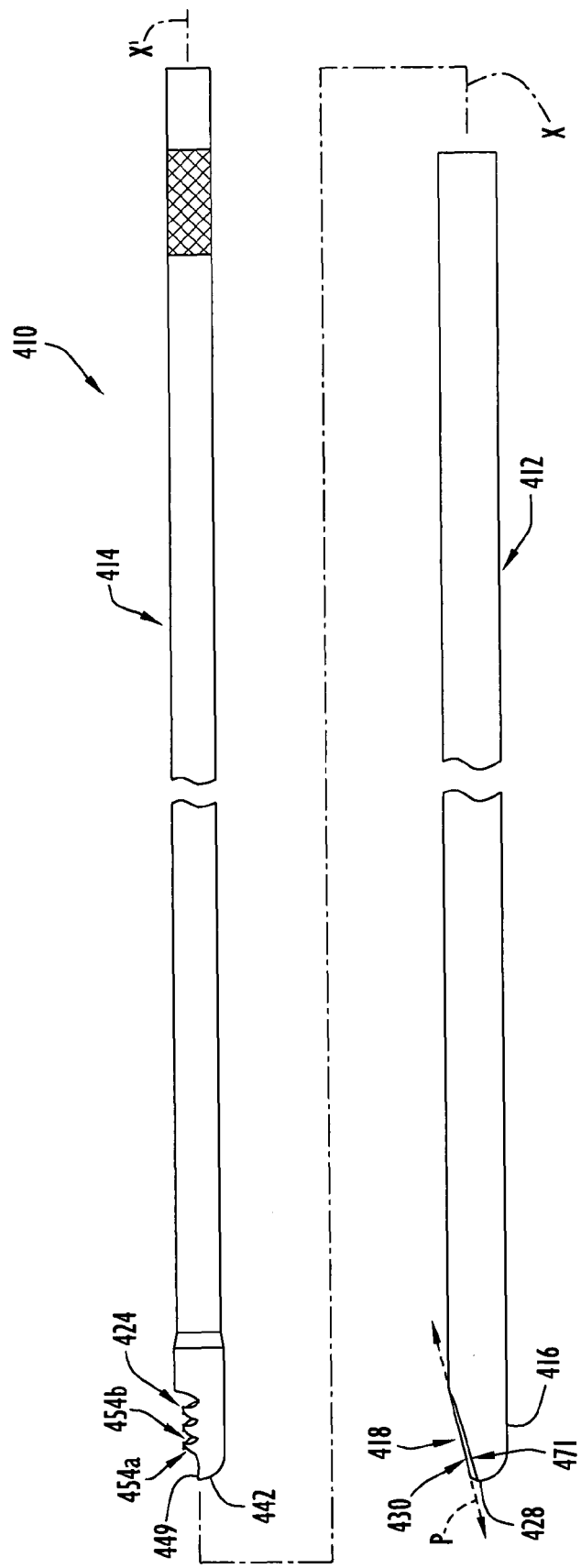
FIG. 12 is an exploded, broken side view of an additional rotary surgical instrument.

An additional and preferred rotary surgical instrument 410 is illustrated in FIG. 12 and comprises outer member 412 and inner member 414. The inner member 414 of rotary surgical instrument 410 is like any of the inner members 14, 114 or 314 described above. The inner member 414 is depicted as being similar to the inner member 14 except that the distal end wall 442 of inner member 414 is of reduced height compared to the distal end wall 42 of inner member 14. In particular, the distal end wall 42 of inner member 14 is seen in FIG. 1 as extending well above the central longitudinal axis X' whereas the distal end wall 442 of inner member 414 is seen in FIG. 12 as not extending above or extending only slightly above the central longitudinal axis X'. In addition, the distal end wall 42 extends above the central longitudinal axis X' to about the same height as the cutting teeth 54a, 54b whereas the distal end wall 442 extends to a height that is well below the height of the cutting teeth 454a, 454b. The cutting teeth 454a, 454b extend along the opposite sides of the aperture 424, and the cutting edge of the inner member 414 may extend or continue along the forward segment 449 of the inner member peripheral surface from one side thereof to the other as is the case for inner member 414.

The outer member 412 is depicted in FIGS. 12-16. The aperture 418 of outer member 412 has a teardrop shaped peripheral configuration, but the aperture 418 could have other peripheral configurations including oval, elliptical and oblong peripheral configurations. The outer member peripheral surface 430 includes an inner peripheral edge 440 at which the outer member peripheral surface 430 meets the internal surface 433 of the outer member 412, and includes an outer peripheral edge 441 extending entirely around the inner peripheral edge 440 in spaced relation therewith. The inner peripheral edge 440 adjoins the internal surface 433 and extends entirely around the outer member aperture 418 to define the peripheral configuration of the outer member aperture. As seen in FIG. 12, the outer member peripheral surface 430 is disposed in an oblique plane P at an acute angle with the central longitudinal axis X of outer member 412. The plane P of the outer member peripheral surface 430 passes through the side and distal end wall 428 of the outer member 412 at an inward angle.

The inner peripheral edge 440 comprises a distal or forward inner peripheral edge segment 451 along the forward segment 435 of peripheral surface 430, a proximal or rearward inner peripheral edge segment 452 along the rearward segment 436 of peripheral surface 430, and opposite side inner peripheral edge segments 455a, 455b along the side segments 434a, 434b of peripheral surface 430 respectively joining opposite ends of the forward inner peripheral edge segment 451 to opposite ends of the rearward inner peripheral edge segment 452. The forward inner peripheral edge segment 451 and the rearward inner peripheral edge segment 452 are each curved or arcuate. The radius of curvature of the forward inner peripheral edge segment 451 is greater than the radius of curvature of the rearward inner peripheral edge segment 452. The forward inner peripheral edge segment 451 is longer in length than the rearward inner peripheral edge segment 452 and is curved in a direction opposite the curvature of the rearward inner peripheral edge segment 452. The side inner peripheral edge segments 455a, 455b extend inwardly toward one another in the proximal direction from the ends of the forward inner peripheral edge segment 451 to the ends of the rearward inner peripheral edge segment 452. The aperture 418 is bisected lengthwise or longitudinally by a bisecting plane P' containing the central longitudinal axis X of the outer member 412. The aperture 418 has a length or longitudinal dimension along the bisecting plane P' between the forward and rearward inner peripheral edge segments 451 and 452. The aperture 418 has a maximum width or lateral dimension, perpendicular to its length, where the opposite ends of the forward inner peripheral edge segment 451 meet the respective side inner peripheral edge segments 455a, 455b. The width of the aperture 418 tapers or narrows in the proximal direction from the maximum width.

The outer peripheral edge 441 of the outer member peripheral surface 430 comprises a distal or forward outer peripheral edge segment 463 along the forward segment 435 of peripheral surface 430, a proximal or rearward outer peripheral edge segment 464 along the rearward segment 436 of peripheral surface 430, opposite side outer peripheral edge segments 465a, 465b along the side segments 434a, 434b of peripheral surface 430 respectively joined to opposite ends of the forward outer peripheral edge segment 463, and transition outer peripheral edge segments 467a, 467b respectively joining the side outer peripheral edge segments 465a, 465b to opposite ends of the rearward outer peripheral edge segment 464. The outer member peripheral surface 430 is planar between the inner peripheral edge 440 and the outer peripheral edge 441 as best seen in FIG. 16. The side outer peripheral edge segments 465a, 465b respectively extend along the side inner peripheral edge segments 455a, 455b in closely spaced relation therewith to define a narrow width portion of the outer member peripheral surface 430 along which the width of the outer member peripheral surface 430 between the inner peripheral edge 440 and the outer peripheral edge 441 is narrow. The narrow width portion of the outer member peripheral surface 430 extends along the side segments 434a, 434b of the peripheral surface 430 and forms a sharp cutting surface or edge 466 on the opposite sides of the aperture 418 providing enhanced cutting effectiveness in combination with the cutting teeth of the inner member 414 as explained further below.

In the case of outer member 412, the forward outer peripheral edge segment 463 extends along the forward inner peripheral edge segment 451 in closely spaced relation therewith, such that the narrow width portion of the outer member peripheral surface 430 and the cutting surface 466 formed thereby extend along the forward segment 435 of peripheral surface 430 from one side segment 434a, 434b to the other. Accordingly, the cutting surface 466 continues along the forward end of the aperture 418 from one side thereof to the other. The forward outer peripheral edge segment 463 and side outer peripheral edge segments 465a, 465b are uniformly spaced from the respective forward inner peripheral edge segment 451 and side inner peripheral edge segments 455a, 455b so that the narrow width portion of peripheral surface 430 is of uniform width.

The transition outer peripheral edge segments 467a, 467b meet the respective side outer peripheral edge segments 465a, 465b at opposed locations or junctions on opposite sides of the central longitudinal axis X. The opposed locations where the transition outer peripheral edge segments 467a, 467b meet the respective side outer peripheral edge segments 465a, 465b are situated near the opposite ends of the rearward inner peripheral edge segment 452. The cutting surface 466 extends continuously, beginning in a distal direction, from one opposed location to the other, and the cutting surface 466 thusly extends substantially entirely around the aperture 418. The transition outer peripheral edge segments 467a, 467b extend from the respective side outer peripheral edge segments 465a, 465b at the opposed locations to meet the opposite ends of the rearward outer peripheral edge segment 464. The transition outer peripheral edge segments 467a, 467b may have a concave curvature in opposite directions from each other between the side outer peripheral edge segments 465a, 465b and the opposite ends of the rearward outer peripheral edge segment 464. The outer member peripheral surface 430 meets the external surface 432 of the outer member 412 along the rearward outer peripheral edge segment 464. The outer member peripheral surface 430 is of greater width at or along the transition outer peripheral edge segments 467a, 467b than along the narrow width portion. The width of the outer member peripheral surface 430 increases further on each side of the bisecting plane P' of the aperture 418 from the width at the transition outer peripheral edge segments 467a, 467b to a maximum width along the bisecting plane P'.

The outer member 412 further comprises a beveled or angled surface 471 extending along the narrow width portion of the peripheral surface 430. In the case of outer member 412, the beveled surface 471 extends along the side outer peripheral edge segments 465a, 465b and forward outer peripheral edge segments 465a, 465b, 463. The beveled surface 471 has opposite ends 473a, 473b that respectively meet the transition outer peripheral edge segments 467a, 467b. The ends 473a, 473b of the beveled surface 471 are each constituted by an end edge that may be angled and/or curving. The end edges of the beveled surface 471 may be respectively formed in whole or in part by the transition outer peripheral edge segments 467a, 467b. The end edges for the beveled surface 471 respectively meet the opposite ends of the rearward outer peripheral edge segment 464 and extend proximally and outwardly beyond the transition outer peripheral edge segments 467a, 467b to meet the external surface 432 of the outer member 412. The beveled surface 471 extends continuously along the outer member peripheral surface 430, beginning in a distal direction, from one end of the beveled surface to the other. The beveled surface 471 thusly extends along the entire or substantially the entire length of the respective side segments 434a, 434b of the peripheral surface 430 and along the entire length of the forward segment 435 of the peripheral surface 430. The beveled surface 471 also extends substantially entirely around the outer member aperture 418.

The beveled surface 471 extends from the outer peripheral edge 441 of the outer member peripheral surface 430 to a border edge 475 at which the beveled surface 471 meets or adjoins the external surface 432 of the outer member 412. The outer peripheral edge 441 along the narrow width portion of the outer member peripheral surface 430 may be considered as defining an inner edge of the beveled surface 471, the ends of which respectively meet the end edges of the beveled surface at the ends 473a, 473b thereof. The border edge 475 of the beveled surface 471 may be considered an outer edge of the beveled surface, the ends of which respectively meet the end edges of the beveled surface at the ends 473a, 473b thereof. As seen in FIG. 16, the beveled surface 471 extends from the outer member peripheral surface 430 to the outer member external surface 432 at an acute angle to the plane of the outer member peripheral surface 430, and the beveled surface 471 is depicted as being planar between the outer member peripheral surface 430 and the outer member external surface 432. The border edge 475 of the beveled surface 471 follows or substantially follows the configuration of the outer peripheral edge segment 441 along the narrow width portion of the outer member peripheral surface 430. The width of the beveled surface 471 between the outer peripheral edge 441 and the border edge 475 is thusly uniform or constant, or is substantially uniform or constant, along the length of the beveled surface from one end thereof to the other. The width of the beveled surface 471 may increase somewhat in the vicinity of the transition outer peripheral edge segments 467a, 467b and/or the ends 473a, 473b of the beveled surface. Depending on the configuration of the end edges at the ends 473a, 473b of the beveled surface 471, the width of the beveled surface may be variable or non-uniform and may taper in a proximal direction at the ends thereof. The width of the beveled surface 471 is depicted as being greater than the width of the narrow width portion of the outer member peripheral surface 430.

The aperture 418 and peripheral surface 430 may initially be formed in the hollow or tubular distal portion 416 of outer member 412 by making a cut through the side and distal end wall of the outer member along plane P. At this point, prior to formation of the beveled surface 471, the peripheral surface 430 will be without the narrow width portion along the forward segment 435 and side segments 434a, 434b thereof and will have an inner peripheral edge adjoining the internal surface 433 and an outer peripheral edge adjoining the external surface 432 along the forward end and opposite sides of the aperture 418. Therefore, the width of the peripheral surface 430 along its forward segment 435 and side segments 434a, 434b prior to formation of the beveled surface 471 will be the full distance between the internal and external surfaces 433, 432 and will be greater than the width thereof following formation of the beveled surface 471. The beveled surface 471 is preferably generated or formed on the outer member 412 through a milling and electrical discharge machining (EDM) process followed by electro-polishing to obtain a uniform finish. Formation of the beveled surface 471 involves removing a portion of the outer member peripheral surface 430 along its forward segment 435 and side segments 434a, 434b and, therefore, along the forward end and opposite sides of the aperture 418, resulting in formation of the narrow width portion as well as the inner edge, the outer edge and the end edges of the beveled surface. The width of the peripheral surface 430 along the narrow width portion thereof no longer extends the full distance between the internal and external surfaces 433, 432 of the outer member 412 but, rather, corresponds to the distance between the internal surface 433 and the beveled surface 471. The presence of the beveled surface 471 and the narrow width portion of the outer member peripheral surface 430 provides a thinner and sharper cutting surface or edge 466 for enhanced cutting effectiveness in cutting anatomical tissue in cooperation with the cutting element of the inner member 414. The enhanced cutting effectiveness enables the instrument 410 to achieve a more aggressive cutting action without requiring the outer member cutting element to have a toothed configuration.

When the inner member 414 is disposed within the outer member 412 in a rotational position where the inner member aperture 424 is in rotational alignment with the outer member aperture 418, the forward segment 449 of the inner member peripheral surface is aligned or flush with or is substantially aligned or flush with, the forward inner peripheral edge segment 451 of the outer member peripheral surface 430. The external surface of the distal end wall 442 of the inner member 414 is in bearing contact with the internal surface of the outer member distal end wall 428. As the inner member 414 is rotated within the outer member 412, anatomical tissue positioned in the outer member aperture 418 is cut by the cutting teeth 454a, 454b cooperating with the side segments 434a, 434b of the outer member peripheral surface 430 and by the forward segment 449 of the inner member peripheral surface cooperating with the forward segment 435 of the outer member peripheral surface 430.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A rotary surgical instrument comprising
   an elongate tubular outer member including a central longitudinal axis, a proximal end, a distal portion, an internal lumen, an aperture in said distal portion establishing communication with said internal lumen, a first cutting edge extending longitudinally on said outer member along a side of said aperture, and a second cutting edge extending longitudinally on said outer member along an opposite side of said aperture; and
   an elongate tubular inner member adapted for being rotatably disposed within said internal lumen of said outer member, said inner member including a central longitudinal axis, a proximal end, a distal portion, an internal lumen, an aperture in said distal portion of said inner member establishing communication with said internal lumen of said inner member, a first row of a series of cutting teeth arranged in succession in the longitudinal direction on said inner member along a side of said aperture in said inner member, and a second row of a series of cutting teeth arranged in succession in the longitudinal direction on said inner member along an opposite side of said aperture in said inner member, each of said cutting teeth having a root, a tip, a convex side that curves convexly from said root to said tip in the longitudinal direction, an opposed side that extends from said root to said tip opposite said convex side, and a cutting edge extending entirely along said convex side from said root to said tip, each of said rows having said cutting teeth arranged in said row with said convex sides of said cutting teeth meeting said opposed sides of next adjacent cutting teeth at said roots of said cutting teeth, said first and second rows of said cutting teeth being moved past said aperture in said outer member when said inner member is rotated about said central longitudinal axis of said inner member within said outer member, said first and second rows of said cutting teeth cooperating with said first and second cutting edges on said outer member to cut anatomical tissue positioned in said aperture in said outer member.

2. The rotary surgical instrument recited in claim 1 wherein said inner member has an external surface and an internal surface, each of said cutting teeth has an external face formed by said external surface and an internal face formed by said internal surface, said convex sides and said opposed sides being disposed between said external and internal faces.

3. The rotary surgical instrument recited in claim 2 wherein said convex sides of said cutting teeth in one of said rows all curve from said roots distally in the longitudinal direction, and said convex sides of said cutting teeth in the other of said rows all curve from said roots proximally in the longitudinal direction.

4. The rotary surgical instrument recited in claim 3 wherein said opposed side of each of said cutting teeth curves convexly from said root to said tip of said cutting tooth in the same direction as the convex curvature of said convex side of said cutting tooth.

5. The rotary surgical instrument recited in claim 4 wherein each of said cutting teeth further has said cutting edge extending along said opposed side of said cutting tooth.

6. The rotary surgical instrument recited in claim 3 wherein said first cutting edge includes a first row of a series of cutting teeth arranged in succession in the longitudinal direction on said outer member along said side of said aperture in said outer member, and said second cutting edge includes a second row of a series of cutting teeth arranged in succession in the longitudinal direction on said outer member along said opposite side of said aperture in said outer member.

7. The rotary surgical instrument recited in claim 6 wherein said cutting teeth of said outer member have a convex curvature in the longitudinal direction.

8. The rotary surgical instrument recited in claim 7 wherein said cutting teeth in one of said rows of cutting teeth on said outer member curve in the same direction as said cutting teeth in said one of said rows of cutting teeth on said inner member, and said cutting teeth in the other of said rows of cutting teeth on said outer member curve in the same direction as said cutting teeth in said other of said rows of cutting teeth on said inner member.

9. The rotary surgical instrument recited in claim 1 wherein said distal portion of said inner member includes a thin-walled tubular part and said cutting teeth are laser cut in said thin-walled tubular part of said distal portion of said inner member.

10. The rotary surgical instrument recited in claim 1 wherein said first and second cutting edges are straight edges.

11. The rotary surgical instrument recited in claim 1 wherein said aperture in said outer member is a side-facing aperture, said outer member includes an external surface, an internal surface defining said internal lumen of said outer member, a peripheral surface extending along said aperture in said outer member and having opposite side segments extending along opposite sides of said aperture in said outer member, said peripheral surface having an inner peripheral edge extending entirely around said aperture in said outer member and adjoining said internal surface, said peripheral surface having an outer peripheral edge extending around said inner peripheral edge in spaced relation therewith, said peripheral surface having a narrow width along said side segments, said side segments defining said first and second cutting edges respectively along said opposite sides of said aperture in said outer member, and said outer member further includes a beveled surface extending along said side segments of said peripheral surface, said beveled surface extending angularly outwardly from said outer peripheral edge to a border edge of said beveled surface adjoining said external surface of said outer member along said side segments of said peripheral surface, said beveled surface being disposed between said peripheral surface and said external surface of said outer member.

12. A rotary surgical instrument comprising
an elongate tubular outer member including a central longitudinal axis, a proximal end, a distal portion, an internal lumen, an aperture in said distal portion establishing communication with said internal lumen, a first cutting edge extending longitudinally on said outer member along a side of said aperture, and a second cutting edge extending longitudinally on said outer member along an opposite side of said aperture; and
an elongate tubular inner member adapted for being rotatably disposed within said internal lumen of said outer member, said inner member including a central longitudinal axis, a proximal end, a distal portion, an internal lumen, an aperture in said distal portion of said inner member establishing communication with said internal lumen of said inner member, a first row of a series of cutting teeth arranged in succession in the longitudinal direction on said inner member along a side of said aperture in said inner member, and a second row of a series of cutting teeth arranged in succession in the longitudinal direction on said inner member along an opposite side of said aperture in said inner member, said cutting teeth of one of said rows having a convex curvature distally in the longitudinal direction of said inner member, and said cutting teeth in the other of said rows having a convex curvature proximally in the longitudinal direction of said inner member, said first and second rows of said cutting teeth being moved past said aperture in said outer member when said inner member is rotated about said central longitudinal axis of said inner member within said outer member, said first and second rows of said cutting teeth cooperating with said first and second cutting edges on said outer member to cut anatomical tissue positioned in said aperture in said outer member.

13. The rotary surgical instrument recited in claim 12 wherein each of said cutting teeth in said one of said rows has a geometric profile defined by a proximal side curving convexly from a root to a tip of said cutting tooth distally in the longitudinal direction and a distal side extending from said root to said tip of said cutting tooth, each of said cutting teeth in said other of said rows has a geometric profile defined by a distal side curving convexly from a root to a tip of said cutting tooth proximally in the longitudinal direction and a proximal side extending from said root to said tip of said cutting tooth, said distal sides of said cutting teeth of said other of said rows having the same convex curvature as said proximal sides of said cutting teeth of said one of said rows.

14. The rotary surgical instrument recited in claim 13 wherein said distal sides of said cutting teeth of said one of said rows curve convexly from said root to said tip of said cutting tooth distally in the longitudinal direction, said proximal sides of said cutting teeth of said other of said rows curve convexly from said root to said tip of said cutting tooth proximally in the longitudinal direction, said proximal sides of said cutting teeth of said other of said rows having the same convex curvature as said distal sides of said cutting teeth of said one of said rows.

15. The rotary surgical instrument recited in claim 13 wherein said tips of said cutting teeth of one of said rows are staggered relative to said tips of said cutting teeth of the other of said rows.

16. The rotary surgical instrument recited in claim 12 wherein said cutting teeth in said one of said rows have a partial crescent-shaped geometric profile curving from said root of said cutting tooth distally in the longitudinal direction, and said cutting teeth in said other of said rows have the same partial crescent-shaped geometric profile but curving from said root of said cutting tooth proximally in the longitudinal direction.

17. The rotary surgical instrument recited in claim 12 wherein said first row extends in the longitudinal direction in parallel with said central longitudinal axis of said inner member, and said second row extends in the longitudinal direction in parallel with said central longitudinal axis of said inner member.

18. The rotary surgical instrument recited in claim 12 wherein said aperture in said outer member is a side-facing aperture, said outer member includes an external surface, an internal surface defining said internal lumen of said outer member, a peripheral surface extending along said aperture in said outer member and having opposite side segments extending along opposite sides of said aperture in said outer member, said peripheral surface having an inner peripheral edge extending entirely around said aperture in said outer member and adjoining said internal surface, said peripheral surface having an outer peripheral edge extending around said inner peripheral edge in spaced relation therewith, said peripheral surface having a narrow width along said side segments, said side segments defining said first and second cutting edges respectively along said opposite sides of said aperture in said outer member, and said outer member further includes a beveled surface extending along said side segments of said peripheral surface, said beveled surface extending angularly outwardly from said outer peripheral edge to a border edge of said beveled surface adjoining said external surface of said outer member along said side segments of said peripheral surface, said beveled surface being disposed between said peripheral surface and said external surface of said outer member.

19. A rotary surgical instrument comprising
an elongate tubular outer member including a central longitudinal axis, a proximal end, a distal portion, an internal lumen, an aperture in said distal portion establishing communication with said internal lumen, a first cutting edge extending longitudinally on said outer member along a side of said aperture, and a second cutting edge extending longitudinally on said outer member along an opposite side of said aperture; and
an elongate tubular inner member adapted for being rotatably disposed within said internal lumen of said outer member, said inner member including a central longitudinal axis, a proximal end, a distal portion, an internal lumen, an aperture in said distal portion of said inner member establishing communication with said internal lumen of said inner member, a first row of a series of cutting teeth arranged in succession in the longitudinal direction on said inner member along a side of said aperture in said inner member, and a second row of a series of cutting teeth arranged in succession in the longitudinal direction on said inner member along an opposite side of said aperture in said inner member, each of said cutting teeth extending from a root to a tip, said tips of said cutting teeth in one of said rows being offset from said tips of said cutting teeth in the other of said rows in a lateral direction transverse to said central longitudinal axis of said inner member, each of said cutting teeth in said one of said rows curving convexly from said root to said tip of said cutting tooth distally in the longitudinal direction, and each of said cutting teeth in said other of said rows curving convexly from said root to said tip of said cutting tooth proximally in the longitudinal direction, said first and second rows of said cutting teeth being moved past said aperture in said outer member when said inner member is rotated about said central longitudinal axis of said inner member within said outer member, said first and second rows of said cutting teeth cooperating with said first and second cutting edges on said outer member to cut anatomical tissue positioned in said aperture in said outer member.

20. The rotary surgical instrument recited in claim 19 wherein each of said cutting teeth in said one of said rows has a cutting edge that extends from said root to said tip of said cutting tooth with a convex curvature distally in the longitudinal direction, and each of said cutting teeth in said other of said rows has a cutting edge that extends from said root to said tip of said cutting tooth with a convex curvature proximally in the longitudinal direction.

21. The rotary surgical instrument recited in claim 19 wherein said first cutting edge comprises a first row of a series of cutting teeth arranged in succession in the longitudinal direction on said outer member along said side of said aperture in said outer member, and said second cutting edge comprises a second row of a series of cutting teeth arranged in succession in the longitudinal direction on said outer member along said opposite side of said aperture in said outer member.

22. The rotary surgical instrument recited in claim 19 wherein said aperture in said outer member is a side-facing aperture, said outer member includes an external surface, an internal surface defining said internal lumen of said outer member, a peripheral surface extending along said aperture in said outer member and having opposite side segments extending along opposite sides of said aperture in said outer member, said peripheral surface having an inner peripheral edge extending entirely around said aperture in said outer member and adjoining said internal surface, said peripheral surface having an outer peripheral edge extending around said inner peripheral edge in spaced relation therewith, said peripheral surface having a narrow width along said side segments, said side segments defining said first and second cutting edges respectively along said opposite sides of said aperture in said outer member, and said outer member further includes a beveled surface extending along said side segments of said peripheral surface, said beveled surface extending angularly outwardly from said outer peripheral edge to a border edge of said beveled surface adjoining said external surface of said outer member along said side segments of said peripheral surface, said beveled surface being disposed between said peripheral surface and said external surface of said outer member.

23. A rotary surgical instrument comprising
an elongate tubular outer member including a central longitudinal axis, a proximal end, a distal portion, an external surface, an internal surface, an internal lumen defined by said internal surface, a side-facing aperture in said distal portion establishing communication with said internal lumen, a peripheral surface extending along said aperture in said outer member and having opposite side segments extending along opposite sides of said aperture, said peripheral surface having an inner peripheral edge extending entirely around said aperture in said outer member and adjoining said internal surface, said peripheral surface having an outer peripheral edge extending around said inner peripheral edge in spaced relation therewith, said peripheral surface having a narrow width along said side segments, said side segments defining a sharp cutting surface extending along said opposite sides of said aperture in said outer member, and said outer member further includes a beveled surface extending along said side segments of said peripheral surface, said beveled surface extending angularly outwardly from said outer peripheral edge to a border edge of said beveled surface adjoining said external surface of said outer member along said side segments of said peripheral surface, said beveled surface being disposed between said peripheral surface and said external surface of said outer member; and
an elongate tubular inner member adapted for being rotatably disposed within said internal lumen of said outer member, said inner member including a central longitudinal axis, a proximal end, a distal portion, an internal lumen, a side-facing aperture in said distal portion of said inner member establishing communication with said internal lumen of said inner member, a first row of a series of cutting teeth arranged in succession in the longitudinal direction on said inner member along a side of said aperture in said inner member, and a second row of a series of cutting teeth arranged in succession in the longitudinal direction on said inner member along an opposite side of said aperture in said inner member, each of said cutting teeth having a root, a tip, and distal and proximal sides extending from said root to meet one another at a sharp point at said tip, at least one of said distal and proximal sides comprising a cutting edge extending from said point to said root with a convex curvature in the longitudinal direction and being sharp enough to shear cut anatomical tissue, said cutting teeth being moved past said aperture in said outer member when said inner member is rotated about said central longitudinal axis of said inner member within said outer member, said first and second rows of said cutting teeth cooperating with said cutting surface of said outer member to cut anatomical tissue positioned in said aperture in said outer member.

24. The rotary surgical instrument recited in claim 23 wherein said peripheral surface of said outer member extends entirely around said aperture in said outer member and is disposed in a plane at an acute angle with said central longitudinal axis of said outer member.

25. The rotary surgical instrument recited in claim 24 wherein said peripheral surface has a forward segment along a forward end of said aperture in said outer member joining said side segments, said peripheral surface having a narrow width along said forward segment further defining said cutting surface along said forward end of said aperture in said outer member.

26. The rotary surgical instrument recited in claim 25 wherein said inner member further includes a cutting edge extending along a forward end of said aperture in said inner member.

27. The rotary surgical instrument recited in claim 24 wherein said beveled surface is planar and is disposed at an acute angle to said plane of said peripheral surface.

* * * * *